US010188310B2

(12) United States Patent
Derichs et al.

(10) Patent No.: US 10,188,310 B2
(45) Date of Patent: Jan. 29, 2019

(54) PROBE FOR DETERMINING MAGNETIC MARKER LOCATIONS

(71) Applicant: Health Beacons, Inc., Concord, MA (US)

(72) Inventors: Kevin J. Derichs, Buda, TX (US); Robert J. Petcavich, The Woodlands, TX (US); Murray A. Reicher, Rancho Santa Fe, CA (US)

(73) Assignee: Health Beacons, Inc., Concord, MA (US)

( * ) Notice: Subject to any disclaimer, the term of this patent is extended or adjusted under 35 U.S.C. 154(b) by 345 days.

(21) Appl. No.: 14/832,528

(22) Filed: Aug. 21, 2015

(65) Prior Publication Data

US 2016/0051164 A1    Feb. 25, 2016

Related U.S. Application Data

(60) Provisional application No. 62/041,132, filed on Aug. 24, 2014.

(51) Int. Cl.
*G01R 33/02* (2006.01)
*A61B 5/05* (2006.01)
(Continued)

(52) U.S. Cl.
CPC ............. *A61B 5/05* (2013.01); *G01R 33/02* (2013.01); *A61B 2034/2051* (2016.02); *A61B 2090/3908* (2016.02); *A61B 2090/3954* (2016.02)

(58) Field of Classification Search
CPC ............. A61B 5/05; A61B 2090/3954; A61B 2090/3908; A61B 2034/2051;
(Continued)

(56) References Cited

U.S. PATENT DOCUMENTS

| 4,142,530 A | 3/1979 | Wittkampf |
| 4,592,356 A | 6/1986 | Gutierrez |

(Continued)

FOREIGN PATENT DOCUMENTS

| EP | 0967927 B1 | 4/2003 |
| WO | WO 98/30166 | 7/1998 |

(Continued)

OTHER PUBLICATIONS

Christopher Konvalin "Compensating for Tilt, Hard-Iron, and Soft-Iron Effects" Sensor Magazine Dec. 1, 2009; accessed online on Nov. 13, 2017; http://www.sensorsmag.com/components/compensating-for-tilt-hard-iron-and-soft-iron-effects.*

(Continued)

*Primary Examiner* — Kaylee R Wilson
(74) *Attorney, Agent, or Firm* — Knobbe Martens Olson & Bear LLP

(57) ABSTRACT

A probe including a first sensor having a first magnetometer and a first accelerometer and a second sensor having a second magnetometer and a second accelerometer is configured for determining the distance and direction to a marker. The marker may be magnetic and may be surgically inserted into a patient's body to mark a specific location. The probe may be used to locate the marker, thus identifying the location. The probe may include a microprocessor that receives an output from the first sensor and an output from the second sensor and determines the distance and direction to the marker.

15 Claims, 24 Drawing Sheets

(51) Int. Cl.
*A61B 34/20* (2016.01)
*A61B 90/00* (2016.01)

(58) Field of Classification Search
CPC ........... A61B 5/065; A61B 5/06; A61B 90/39; A61B 5/064; A61B 5/062; G01R 33/02; G01R 33/0017; A01K 11/006; G06K 2007/10524; G06K 7/10386
USPC .......................................................... 600/409
See application file for complete search history.

(56) References Cited

U.S. PATENT DOCUMENTS

| | | |
|---|---|---|
| 4,809,713 A | 3/1989 | Grayzel |
| 4,874,375 A | 10/1989 | Ellison |
| 4,886,049 A | 12/1989 | Darras |
| 5,011,473 A | 4/1991 | Gattuma |
| 5,059,197 A | 10/1991 | Urie et al. |
| 5,099,845 A | 3/1992 | Besz et al. |
| 5,127,916 A | 7/1992 | Spencer et al. |
| 5,158,084 A | 10/1992 | Ghiatas |
| 5,197,482 A | 3/1993 | Rank |
| 5,221,269 A | 6/1993 | Miller et al. |
| 5,284,128 A | 2/1994 | Hart |
| 5,325,873 A | 7/1994 | Hirschi |
| 5,409,004 A | 4/1995 | Sloan |
| 5,709,697 A | 1/1998 | Ratcliff et al. |
| 5,864,323 A | 1/1999 | Berthon |
| 5,925,935 A | 9/1999 | Mejia et al. |
| 5,967,968 A | 10/1999 | Nishioka |
| 5,989,265 A | 11/1999 | Boquet De La Joliniere et al. |
| 6,018,094 A | 1/2000 | Fox |
| 6,026,818 A | 2/2000 | Blair et al. |
| 6,161,034 A | 12/2000 | Burbank et al. |
| 6,173,175 B1 | 1/2001 | Sinanan et al. |
| 6,173,715 B1 | 1/2001 | Sinanan |
| 6,184,777 B1 | 2/2001 | Mejia |
| 6,239,724 B1 | 5/2001 | Doron et al. |
| 6,261,247 B1 | 7/2001 | Ishikawa et al. |
| 6,363,940 B1 | 4/2002 | Krag |
| 6,398,710 B1 | 6/2002 | Ishikawa et al. |
| 6,402,037 B1 | 6/2002 | Prasad et al. |
| 6,427,081 B1 | 7/2002 | Burbank et al. |
| 6,443,980 B1 | 9/2002 | Wang et al. |
| 6,496,717 B2 | 12/2002 | Cox et al. |
| 6,567,689 B2 | 5/2003 | Burbank et al. |
| 6,611,141 B1 | 8/2003 | Schulz et al. |
| 6,698,433 B2 | 3/2004 | Krag |
| 6,995,729 B2 | 2/2006 | Govari et al. |
| 7,026,941 B1 | 4/2006 | Anderson |
| 7,195,629 B2 | 3/2007 | Behl et al. |
| 8,113,210 B2 | 2/2012 | Petcavich et al. |
| 8,353,917 B2 | 1/2013 | Mandecki et al. |
| 8,939,153 B1 | 1/2015 | Reicher et al. |
| 8,973,584 B2 | 3/2015 | Brander et al. |
| 2001/0020148 A1 | 9/2001 | Sasse et al. |
| 2002/0046756 A1 | 4/2002 | Laizzo et al. |
| 2002/0107445 A1 | 8/2002 | Govari |
| 2002/0170591 A1 | 11/2002 | Armer et al. |
| 2003/0004411 A1 | 1/2003 | Govari et al. |
| 2003/0018246 A1 | 1/2003 | Govari et al. |
| 2003/0018353 A1 | 1/2003 | Yang et al. |
| 2003/0023161 A1 | 1/2003 | Govari et al. |
| 2003/0062988 A1 | 4/2003 | Mandecki et al. |
| 2003/0063351 A1 | 4/2003 | Mandecki et al. |
| 2003/0120150 A1 | 6/2003 | Govari |
| 2004/0030379 A1 | 2/2004 | Hamm et al. |
| 2004/0087914 A1 | 5/2004 | Bryan et al. |
| 2004/0092965 A1 | 5/2004 | Parihar |
| 2004/0236193 A1 | 11/2004 | Sharf |
| 2005/0033108 A1 | 2/2005 | Sawyer |
| 2005/0165305 A1 | 7/2005 | Foerster et al. |
| 2005/0242177 A1 | 11/2005 | Roberge et al. |
| 2005/0272977 A1 | 12/2005 | Saadat et al. |
| 2006/0084865 A1 | 4/2006 | Burbank et al. |
| 2006/0097847 A1 | 5/2006 | Bervoets et al. |
| 2006/0117859 A1 | 6/2006 | Liu et al. |
| 2006/0155190 A1 | 7/2006 | Burbank et al. |
| 2006/0184396 A1 | 8/2006 | Dennis et al. |
| 2006/0208896 A1 | 9/2006 | Mason |
| 2006/0241396 A1 | 10/2006 | Fabian et al. |
| 2006/0258933 A1 | 11/2006 | Ellis et al. |
| 2006/0271096 A1 | 11/2006 | Hamada |
| 2007/0016009 A1 | 1/2007 | Lakin |
| 2007/0249901 A1 | 10/2007 | Ohline et al. |
| 2008/0086046 A1 | 4/2008 | Petcavich |
| 2008/0281190 A1 | 11/2008 | Petcavich et al. |
| 2009/0081461 A1 | 3/2009 | Yi et al. |
| 2009/0131825 A1 | 5/2009 | Burbank et al. |
| 2010/0249576 A1* | 9/2010 | Askarinya ................ A61B 5/06 600/424 |
| 2011/0071362 A1 | 3/2011 | Reicher |
| 2011/0071387 A1 | 3/2011 | Petcavich et al. |
| 2011/0077659 A1 | 3/2011 | Mandecki et al. |
| 2012/0277752 A1 | 11/2012 | Wasielewski |
| 2014/0018663 A1 | 1/2014 | Harmer et al. |
| 2014/0106470 A1 | 4/2014 | Kopacka et al. |
| 2014/0257104 A1* | 9/2014 | Dunbar ................ A61B 8/4254 600/443 |
| 2017/0189634 A1* | 7/2017 | Larson .............. A61M 16/0488 |

FOREIGN PATENT DOCUMENTS

| | | |
|---|---|---|
| WO | WO 2007/087447 | 8/2007 |
| WO | WO 2007/117478 | 10/2007 |

OTHER PUBLICATIONS

Written Opinion of the International Searching Authority in International Application No. PCT/US2015/046409, dated Nov. 27, 2015.
p-Chips for Life Science and Diagnostic Applications; http://www.pharmaseq.com/index.php/technology/pchipsforlifesciencediagnosticapplications; printed Jan. 2014; PharmaSeq, Inc.; 1 page.
"Tagging of Laboratory Mice Using Electronic p-Chips", Pharmaseq, Inc. White Paper; www.pharmaseq.com; 2012; accessed Jan. 2014; 8 pages.
Reicher, Joshua et al.; "Use of Radio Frequency Identification (RFID) Tags in Bedside Monitoring of Endotracheal Tube Position"; Journal of Clinical Monitoring and Computing, Jun. 2007;21:155-8; reformatted into 5 pages.
Reicher, Joshua et al.; "Radiofrequency Identification Tags for Preoperative Tumor Localization: Proof of Concept", Women's Imaging Original Research; Nov. 2008; pp. 1359-1365.
Ozyagcilar, Talat. "Implementing a Tilt-Compensated eCompass using Accelerometer and Magnetometer Sensors." http://cache.freescale.com/files/sensors/doc/app_note/AN4248.pdf. Freescale Semiconductor, Nov. 2015, pp. 1-21, Rev. 4.0. Document No. AN4248.
Ozyagcilar, Talat. "Layout Recommendations for PCBs Using a Magnetometer Sensor." http://cache.freescale.com/files/sensors/doc/app_note/AN4247.pdf. Freescale Semiconductor, Nov. 2015, pp. 1-13, Rev. 4.0, Document Number Document No. AN4247.
Ozyagcilar, Talat. "Calibrating an eCompass in the Present of Hard- and Soft-Iron Interference." http://cache.freescale.com/files/sensors/doc/app_note/AN4246.pdf. Freescale Semiconductor, Nov. 2015, pp. 1-18, Rev. 4.0, Document No. AN4246.
http://www.vectornav.com/support/library/magnetometer. VectorNav Technologies, LLC printed on Jul. 29, 2015.

* cited by examiner

Magnetometer
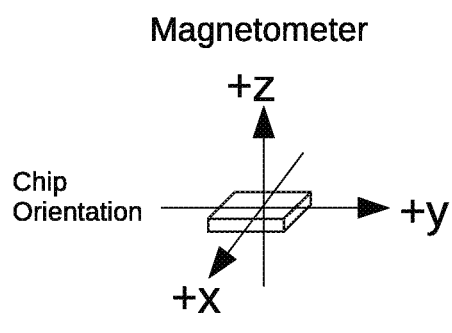
Chip Orientation
Accelerometer (Gravity)
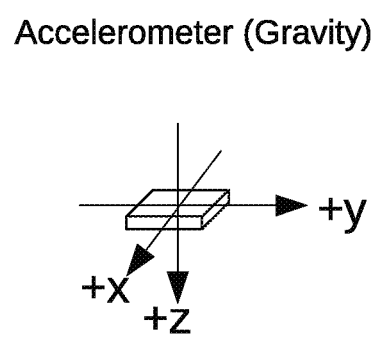
Influence
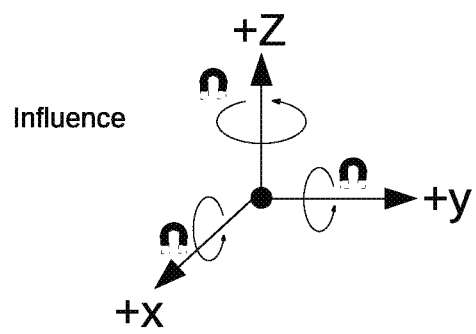
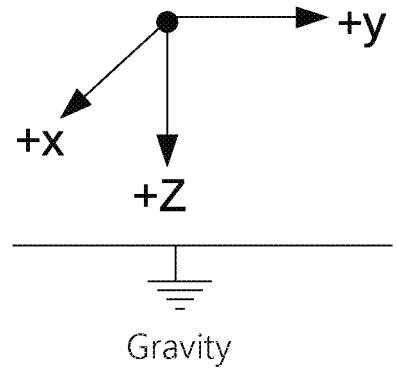
Gravity
FIG. 3A            FIG. 3B

| Before Balancing | | Balance Routine | |
|---|---|---|---|
| Magnetometer | | Measured Raw Data | |
| | | min | max |
| Base Sensor Pair Data | x | -431 | 981 |
| | y | -864 | 962 |
| | z | -1601 | -231 |
| Tip Sensor Pair Data | x | -1210 | 309 |
| | y | -1181 | 1095 |
| | z | -315 | 1054 |

FIG. 6A

| Gain & Offset Calculation | | Individual Length | Gain<br>Average Length /<br>Individual Length | Offset |
|---|---|---|---|---|
| Magnetometer | | | | |
| Base Sensor Pair Data | | Abs(min) + Abs (max) | | ((max-min) /2)+min |
| | x | 1412 | 1.153 | 275 |
| | y | 1826 | 0.892 | 49 |
| | z | 1370 | 1.189 | -916 |
| Tip Sensor Pair Data | | | | |
| | x | 1519 | 1.072 | -450.5 |
| | y | 2276 | 0.716 | -43 |
| | z | 1369 | 1.190 | 369.5 |
| | | Sum (Base xyz & Tip xyz) | | |
| | | 9772 | | |
| | | Average Length | | |
| | | 1628.667 | | |

FIG. 6B

| After Balancing | | min Offset adjusted | max Offset adjusted | min Gain Corrected | max Gain Corrected |
|---|---|---|---|---|---|
| Base Sensor Pair Data | x | -706 | 706 | -814 | 814 |
| | y | -913 | 913 | -814 | 814 |
| | z | -685 | 685 | -814 | 814 |
| Tip Sensor Pair Data | x | -760 | 760 | -814 | 814 |
| | y | -1138 | 1138 | -814 | 814 |
| | z | -685 | 685 | -814 | 814 |

FIG. 8

Example Measurement of a Target Magnet 17.1 mm to the Tip Sensor

| | | Raw Data | Data After Offset adjusted | Data After Gain Corrected |
|---|---|---|---|---|
| Base Sensor Pair Data | x | 982 | 707 | 815 |
| | y | -454 | -503 | -449 |
| | z | -840 | 76 | 90 |
| Tip Sensor Pair Data | x | -97 | 354 | 379 |
| | y | -1974 | -1931 | -1385 |
| | z | 274 | -96 | -114 |

| | Differential | Differential / 32768 *12 | Pythagorean theorem | Zero Adjust | Lookup Value |
|---|---|---|---|---|---|
| | | | Magnitude = | | mm |
| | | | Sqrt( x^2 + y^2 + z^2) | 0.309 | 17.1 |
| x | 436.465 | 0.160 | | | |
| y | 933.149 | 0.342 | 0.385 | | |
| z | 203.963 | 0.075 | | | |

FIG. 11

Look-up Table to Convert Field Strength to Distance

| Field Strength | Bx | unknown | gauss |
|---|---|---|---|
| radius | R | 0.5 | mm |
| length | L | 4 | mm |
| Residual Inductance | Br | 4200 | |
| Distance | X | 0 | mm |
| step size | ss | 0.1 | mm |
| Calculation | | | |
| Bx=(Br/2)*(((L + X ) / (Sqrt(R^2+(L+X)^2))) - (X/(Sqrt(R^2+X^2)))) | | | |

| Field strength to Distance Calculation Breakdown | | | | | | | |
|---|---|---|---|---|---|---|---|
| Distance (mm) | Br/2 | L+X | R*R | (L+X)^2 | Distance (mm) | Sqrt ((R^2)+ (X^2)) | Bx |
| 0.0 | 2100 | 4.0 | 0.25 | 16.00 | 0.0 | 0.500 | 2083.784 |
| 0.1 | 2100 | 4.1 | 0.25 | 16.81 | 0.1 | 0.510 | 1672.712 |
| 0.2 | 2100 | 4.2 | 0.25 | 17.64 | 0.2 | 0.539 | 1305.355 |
| 0.3 | 2100 | 4.3 | 0.25 | 18.49 | 0.3 | 0.583 | 1005.504 |
| 0.4 | 2100 | 4.4 | 0.25 | 19.36 | 0.4 | 0.640 | 774.711 |
| 0.5 | 2100 | 4.5 | 0.25 | 20.25 | 0.5 | 0.707 | 602.232 |
| 16.6 | 2100 | 20.6 | 0.25 | 424.36 | 16.6 | 16.608 | 0.334 |
| 16.7 | 2100 | 20.7 | 0.25 | 428.49 | 16.7 | 16.707 | 0.328 |
| 16.8 | 2100 | 20.8 | 0.25 | 432.64 | 16.8 | 16.807 | 0.323 |
| 16.9 | 2100 | 20.9 | 0.25 | 436.81 | 16.9 | 16.907 | 0.318 |
| 17.0 | 2100 | 21.0 | 0.25 | 441.00 | 17.0 | 17.007 | 0.313 |
| 17.1 | 2100 | 21.0 | 0.25 | 445.21 | 17.1 | 17.107 | 0.308 |
| 17.2 | 2100 | 21.2 | 0.25 | 449.44 | 17.2 | 17.207 | 0.303 |
| 17.3 | 2100 | 21.3 | 0.25 | 453.69 | 17.3 | 17.307 | 0.298 |
| 17.4 | 2100 | 21.4 | 0.25 | 457.96 | 17.4 | 17.407 | 0.294 |
| 17.5 | 2100 | 21.5 | 0.25 | 462.25 | 17.5 | 17.507 | 0.289 |
| 17.6 | 2100 | 21.6 | 0.25 | 466.56 | 17.6 | 17.607 | 0.285 |
| 17.7 | 2100 | 21.7 | 0.25 | 470.89 | 17.7 | 17.707 | 0.280 |

FIG. 12A xyz Magnetometer Sensor Balancing Calculations for Gain and Offset

Before Balancing

| Base Sensor Pair Data | | Balance Routine Measured Raw Data | | | Individual Length | Gain | Offset | | After Balancing | | | |
|---|---|---|---|---|---|---|---|---|---|---|---|---|
| | | min | max | | Abs (min) + Abs (max) | Average Length / Individual Length | ((max-min)/2) + min | | min Offset adjusted | max Offset adjusted | min Gain Corrected | max Gain Corrected |
| x | | -431 | 981 | x | 1412 | 1.153 | 275 | x | -706 | 706 | -814 | 814 |
| y | | -864 | 962 | y | 1826 | 0.892 | 49 | y | -913 | 913 | -814 | 814 |
| z | | -1601 | -231 | z | 1370 | 1.189 | -916 | z | -685 | 685 | -814 | 814 |

| Tip Sensor Pair Data | | min | max | | | | | | | | | |
|---|---|---|---|---|---|---|---|---|---|---|---|---|
| x | | -1210 | 309 | x | 1519 | 1.072 | -450.5 | x | -760 | 760 | -814 | 814 |
| y | | -1181 | 1095 | y | 2276 | 0.716 | -43 | y | -1138 | 1138 | -814 | 814 |
| z | | -315 | 1054 | z | 1369 | 1.190 | 369.5 | z | -685 | 685 | -814 | 814 |

Sum (Base xyz & Tip xyz) 9772
Average Length 1628.667

FIG. 12B

Example #1 (7.1 mm Distance)
Target Magnet Raw Data Measurement and Correction for Offset and Gain

| | Raw Data | Data After Offset adjusted | Data After Gain Corrected | | Differential | Differential / 32768*12 | Pythagorean theorem Magnitude = Sqrt(x^2 + y^2 + z^2) | Zero Adjust | Lookup Value mm |
|---|---|---|---|---|---|---|---|---|---|
| x | 917 | 642 | 741 | | | | | | |
| y | -541 | -590 | -526 | | | | | | |
| z | -922 | -6 | -7 | | | | | | |
| x | -3611 | -3161 | -3389 | | 4129.190 | 1.512 | | | |
| y | 8987 | 9030 | 6462 | | -6987.953 | -2.559 | 3.146 | 3.146 | 7.1 |
| z | 2728 | 2359 | 2806 | | -2812.984 | -1.030 | | | |

FIG. 12C

Example #2 (12.0 mm Distance)

Target Magnet Raw Data Measurement and Correction for Offset and Gain

| | Raw Data | Data After Offset adjusted | Data After Gain Corrected | | | | |
|---|---|---|---|---|---|---|---|
| x | 966 | 691 | 797 | | | | |
| y | -481 | -530 | -473 | | | | |
| z | -825 | 92 | 109 | | | | |
| | | | | Differential | Differential / 32768*12 | Pythagorean theorem Magnitude = Sqrt(x^2 + y^2 + z^2) | Zero Adjust | Lookup Value mm |
| x | 290 | 741 | 794 | 3.070 | 0.0011 | | | |
| y | -3553 | -3510 | -2512 | 2038.972 | 0.7467 | 0.880 | 0.908 | 12.0 |
| z | 1530 | 1161 | 1381 | -1271.249 | -0.4655 | | | |

FIG. 12D

Accelerometer Use to Calculate Pitch, Roll, & Yaw

Yaw = arctan2( y / x )
Pitch = arctan2( x / z )
Roll = arctan2( y / z )

US 10,188,310 B2

PROBE FOR DETERMINING MAGNETIC MARKER LOCATIONS

CROSS-REFERENCE TO RELATED APPLICATIONS

This application is non-provisional and claims the priority benefit under 35 U.S.C. § 119(e) of U.S. Provisional Application No. 62/041,132, filed on Aug. 24, 2014, and titled "MAGNETIC MARKER, SCANNING DEVICE, AND METHODS OF PERFORMING SURGERY USING THE SAME," which is hereby incorporated by reference in its entirety.

BACKGROUND

Marking potentially cancerous tissue for subsequent surgical removal, such as marking a lesion in breast tissue for later removal in a lumpectomy procedure, remains a big challenge for the health care system. It is desirable to place tissue markers at locations of interest in patients, sometimes deep within a patient's tissue, that are both small and easily detectable by some type of external scanning device. In addition, any markers that are placed in the body should have a minimal or no MRI image footprint that may obscure anatomical features (e.g., tumors) that may be located in the imaged area. Another important consideration is the complexity of inserting such markers, which vary in size and detection range, so as to minimize pain and discomfort during the procedure.

SUMMARY

The systems, methods, and devices described herein each have several aspects, no single one of which is solely responsible for its desirable attributes. Without limiting the scope of this disclosure, several non-limiting features will now be discussed briefly.

In one aspect, a probe for detecting a magnetic marker includes a first sensor, including a first magnetometer and a first accelerometer located in a handheld housing, a second sensor, including a second magnetometer and a second accelerometer, the second sensor located in the housing and separated from the first sensor, and a processor located in the housing and electrically connected to the first sensor and the second sensor, the processor configured to receive an output from the first sensor and an output from the second sensor and determine a distance and direction between one of the first sensor and the second sensor and a magnetic marker.

In some embodiments, the first and the second magnetometers are configured to detect the field strength of the magnetic field of a magnetic maker within a range measured from each of the first and second magnetometers. The first and second sensors may be separated by a distance greater than the range. In some embodiments, the distance separating the first and second sensors is at least twice the range of the first and second magnetometers, such that the field strength of the magnetic field of a magnetic marker can only be substantially detected by either the first magnetometer or the second magnetometer.

In some embodiments, the processor is configured to determine the distance between one of the first sensor and the second sensor and a magnetic marker by calculating a difference between the output of the first sensor and the output of the second sensor. The difference may represent the field strength of the magnetic marker.

In some embodiments, the probe also includes a memory configured to store a lookup table containing data relating the magnetic field strength of a magnetic marker to a distance from the magnetic marker.

In some embodiments, the housing of the probe is configured as a wand and includes a base, wherein the first sensor is located in the base, an extension member extending from the base, the extension member defining the distance between the first and second sensors, and a tip, wherein the second sensor is located in the tip, and wherein the processor determines the distance and direction between the tip and the magnetic marker.

In another aspect, a method for determining the distance and direction between a probe and a magnetic marker includes providing a probe which includes a first sensor, having a first magnetometer and a first accelerometer, and a second sensor, having a second magnetometer a second accelerometer, the probe configured to determine the position in three-dimensional space of a magnetic marker, balancing the probe while away from the magnetic marker, moving the balanced probe so that the magnetic marker is within a range of the magnetic marker, and determining the distance and direction between the probe and the magnetic marker by comparing an output of the first sensor with an output of the second sensor.

In some embodiments, balancing the probe includes compensating for a gain and an offset in the output of the first magnetometer and the output of the second magnetometer, wherein the gain and the offset are caused by hard and soft iron effects. In some embodiments, the output of each of the first and second magnetometers comprises X, Y, and Z, values, and balancing the probe further includes rotating the probe through 360 degrees around each of three orthogonal axes. In some embodiments, balancing also includes, for each of the first and second magnetometers, recording the minimum and maximum X, Y, and Z values output during the rotation, calculating a length between the minimum and maximum values for each of X, Y, and Z, calculating a gain factor by dividing the length for each of X, Y, and Z by the average length of the X, Y, and Z for both magnetometers, and calculating an offset value for each of X, Y, and Z by, for each of X, Y, and Z, adding half the length of X, Y, and Z, to the minimum value for X, Y, and Z. In some embodiments, the method includes adjusting raw output data into balanced output data by subtracting the offset value and then multiplying the result by the gain factor for each of X, Y, and Z.

In some embodiments of the method, the output of the first sensor comprises first magnetometer output data and first accelerometer output data, and the output of the second sensor comprises second magnetometer output data and second accelerometer output data, and wherein determining the distance and direction between the probe and the magnetic marker further includes calculating a difference between the first magnetometer output data and the second magnetometer output data to determine distance between the probe and the magnetic marker, and determining the orientation of the probe using one of the first accelerometer data or the second accelerometer data.

BRIEF DESCRIPTION OF THE DRAWINGS

The features of this disclosure will become more fully apparent from the following description and appended claims, taken in conjunction with the following figures.

FIGS. 3A and 3B show the three axes for each of the magnetometer and accelerometer, respectively, in a sensor pair.

FIG. 6A is a table containing sample magnetometer output data obtained during the probe balancing process and FIG. 6B is a table which presents calculations of the gain and offset values used during the balancing process using the sample data of FIG. 6A.

FIG. 8 is a table containing sample balanced data. The data in the table represents the raw data of FIG. 6A in balanced form.

FIG. 11 provides tables showing sample data in both raw and balanced form that is representative of a marker positioned within range of the tip sensor pair. It further illustrates calculation of the magnitude of the magnetic field strength of a marker using that data.

FIG. 12A provides an example of a lookup table which relates the magnetic field strength of a marker to a distance to that marker.

FIG. 12B through 12D provide a table of another set of sample data and the calculation of gain and offset values used to balance a probe, according to one embodiment, as well as two example measurements that are calculated with the probe at different distances from a marker.

DETAILED DESCRIPTION

Example System Overview

Figure 1:
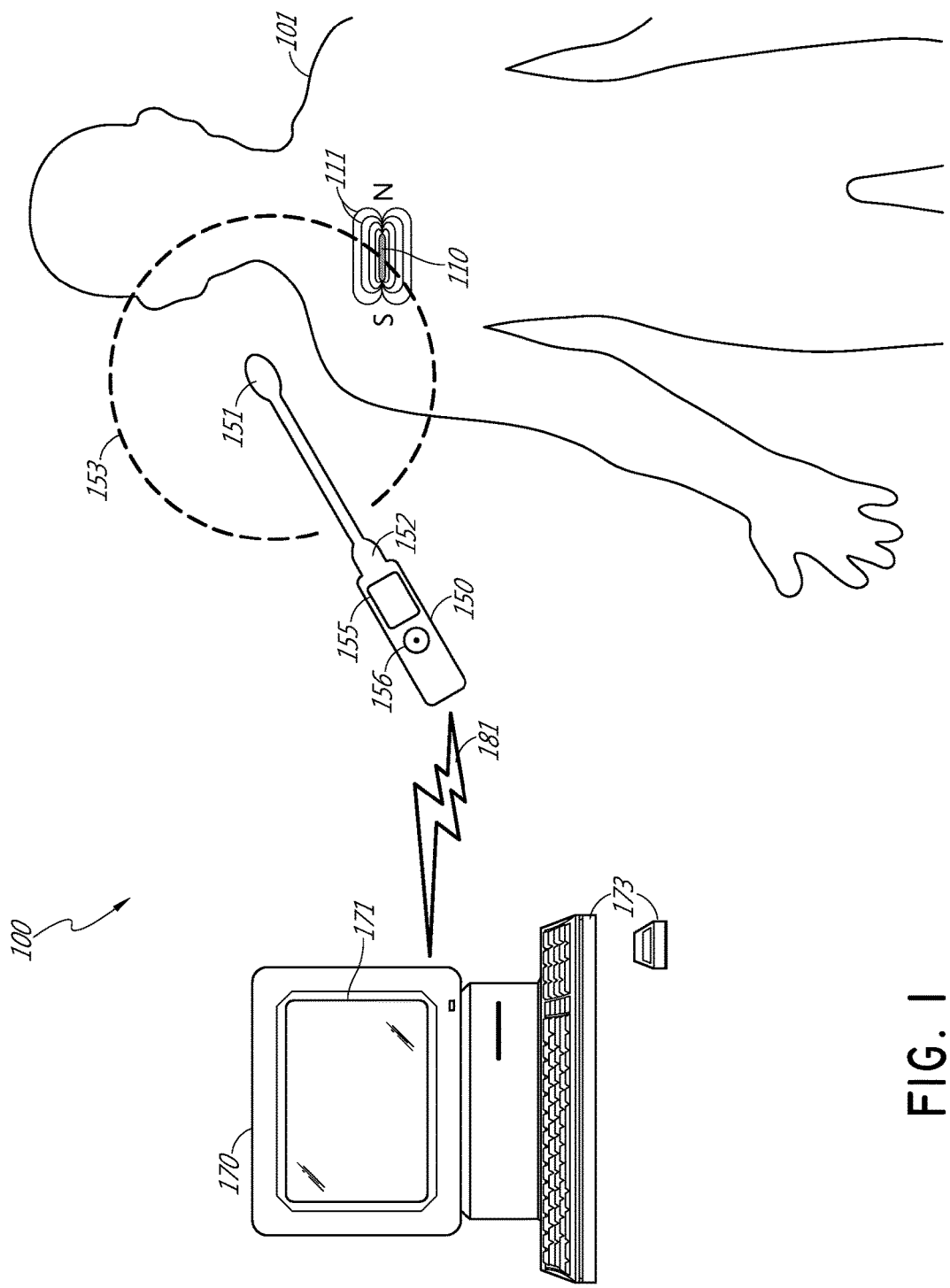
FIG. 1 illustrates an example system for detecting the position of a marker within a patient's body using a handheld probe, according to one embodiment.

FIG. 1 illustrates an example system 100 for determining the position of a marker 110 within a patient's body 101 using a handheld probe 150, according to one embodiment. In this example a marker 110 is embedded in tissue of a patient 101 and a probe 150 is used to identify the marker 110 without insertion into tissue, such as by moving across the skin of the patient 101 in areas near where the marker 110 is believed to be located. In this example, an external device 170, such as a computer, mobile phone, or tablet, is illustrated in communication with the probe 150. In some embodiments, the probe 150 operates independent of any external device 170 and/or doesn't require any external device 170. As used herein, "the system" or "the system 100" includes one or more of various components that may be used to place and/or locate markers within mammalian tissue. For example, in one embodiment, the system 100 includes the handheld probe 150 and one or more markers 110, and in other embodiments the system 100 also includes the external device 170.

As will be described more fully herein, the marker 110 may be surgically inserted into a patient's body 101 to mark the location of tissue, for example, potentially cancerous breast tissue (or any other tissue), for removal. In some embodiments, the marker 110 is inserted into the body via a natural opening or a surgical opening. The probe 150 may then be used to determine the location of the marker 110 within the patient's body 101. In the embodiment of FIG. 1, the probe 150 includes a tip sensor pair 151 configured to communicate with one or more microprocessors to sense and determine the distance and direction to the marker 110 within a range 153 of the sensing tip 164 of the probe 150. The distance and direction to the marker 110 may be shown to a user on a display 155, indicated audibly using a speaker 156, and/or relayed to the external device 170 and shown on a display 171 thereof.

In this embodiment, the marker 110 comprises a magnet, such as a magnet with a bio-compatible coating/layer surrounding the magnet or simply a magnet. In some embodiments, the marker 110 is a micro magnet that has a strong magnetic field relative to its size. For example, the magnet may be a neodymium rare earth magnet, or may comprise other magnetic materials such as ferrite, samarium cobalt, yttrium cobalt, and combinations thereof. Various other types of magnets can be used in conjunction with the probe 150. In some embodiments, the probe 150 must be balanced with reference to the specific characteristics of the particular magnet. In some embodiments, the marker 110 has a magnetic field strength in the range of between about 1,000 to about 20,000 Gauss. A magnetic field strength of approximately 5,000 Gauss may be preferred in some applications. These field strength ranges are provided for example only—other field strengths may be used. The example magnetic field strength calculations herein are presented in units of Gauss, although units of Tesla may also be used in some embodiments. The conversion factor is 1 Tesla equals 10,000 Gauss.

The marker 110 can comprise various geometric shapes, such as spheres, rods, rings, discs, cylinders, and blocks, among others. In one embodiment, the marker 110 is configured as a micro rod having a diameter from about 0.2 mm to about 2.0 mm, with about 0.75 mm to about 1.5 mm being preferred in some applications. A marker 110 configured as a micro rod may have a length of about 1 mm to about 3 mm, with about 2 mm being preferred in some applications.

These size ranges are provided as examples; other size ranges and shapes of the marker 110 may also be used with the system 100. In some embodiments, the marker 110 is configured to be as small as possible, for ease of insertion into the patient's body 101 and precision of marking, while still having a magnetic field strength sufficiently strong to be detected by the probe 150 external to the patient's body 101.

In FIG. 1, the marker 110 is illustrated as a micro rod magnet (not shown to scale with reference to other objects in FIG. 1). The magnet has north and south poles on opposing ends of the micro rod. The shape of the magnetic field of such a marker 110 is illustrated with magnetic field lines 111 in the figure. In general, the magnetic field lines 111 form loops extending between the north and south poles of the magnet. Markers 110 with other magnetic field shapes may be used with probe 150 according to the principles described herein.

In some embodiments, the marker 110 is gold coated. A gold coating may increase the biocompatibility of the marker 110. In some embodiments, the coating may be omitted.

In some embodiments, the marker 110 includes an anti-migration device. The anti-migration device may be configured to ensure that the marker 110 remains in the position in which it is placed. For example, the anti-migration device could include a hook or anchor, such as is described in U.S. Pat. No. 8,939,153, issued on Jan. 27, 2015, and entitled "Transponder Strings," which is hereby incorporated by reference in its entirety and for all purposes. In some embodiments, a collagen plug or sleeve may encapsulate, or partially encapsulate, the marker 110. The collagen plug or sleeve may resist migration of the marker 110 after the marker 110 is implanted into the patient's body.

In use, one or more markers 110 may be loaded into a syringe that can penetrate mammalian tissue to a depth of about 0.5 mm to about 300 millimeters depending on the type of tissue and the depth of the tissue to be marked. The system 100 may have particularly beneficial application in marking breast tumors, which can range in depth from between about 0.1 mm to about 75 mm or more, although, the system 100 is not limited to this application. Using the syringe, the markers 110 may be inserted into or near the tumorous tissue to be marked using ultrasound, CAT scanning or MRI real time imaging. This allows the markers 110 to be accurately placed, as the medical professional inserting the markers 110 is able to see the location of the tumor and marker 110 in real time. However, placement of the markers 110 often occurs hours, days, or weeks prior to the subsequent surgical procedure wherein the markers 110 are located and the surrounding tissue is examined (and possibly biopsied in the case of a tumor). During surgical removal of the tumorous tissue it is generally not possible to use ultrasound, CAT scanning or MRI imaging in the operating room. Thus, use of the probe 150 is desirable as it is allows the location of the tumorous tissue to be accurately determined by detecting the location of the marker 110.

In some embodiments, the marker 110 can be injected along with a conventional non-magnetic marker. In some cases where the marker 110 is injected along with a conventional non-magnetic marker, the marker 110 can be connected to a suture, such as 2-0 proline with the suture extending to the skin surface and then covered with a sterile dressing. If the biopsy is found to be negative, the doctor could remove the suture and marker 110, leaving behind the conventional marker. This would allow use of the marker 110 for all or most biopsies, knowing that the magnet could be removed if a surgical excision is not required based on a negative biopsy result. Similarly, in some embodiments, the marker 110 could be implanted connected to a suture as described above, but the suture could extend to another marker 110 or RFID that is left subcutaneously. If the biopsy is negative, the two magnets could be easily removed together, because embodiments of the present system could be used to locate the subcutaneous marker 110.

In some embodiments, multiple magnetic markers and/or other tags may be included in a string of markers, such as connected via a suture, with one of the markers near the lesion of interest and one near the skin surface so it may be more easily located, possibly with one or more markers in between. For example, magnetic markers may be included in the various configurations of markers disclosed in U.S. Pat. No. 8,939,153, issued on Jan. 27, 2015, and entitled "Transponder Strings," which is hereby incorporated by reference in its entirety and for all purposes. For example, any of the transponders mentioned in that patent may be replaced with a magnetic marker and located using the probe 150 discussed herein.

In some embodiments, the marker 110 is attached to an RFID or light based chip (such as a Pharmaseq) so that the marker 110 is essentially labeled with a serial number. This may be useful for differentiating between multiple markers 110.

The probe 150 will be described in greater detail below. However, in general, the probe 150 may include at least some of the following features: a battery, a microprocessor, wireless communications capability, and at least two magnetometers/accelerometers, a reference magnetometer/accelerometer and a sensing magnetometer/accelerometer. As used herein, a pair of magnetometer/accelerometer sensors, whether both sensors are on a single chip or multiple chips (e.g., an EEPROM, FPGA, ASIC, or other chip), may be referred to as a "sensor pair," such as a "base sensor pair" and a "tip sensor pair." In a preferred embodiment, the probe 150 is configured to determine the location in three-dimensional space of the marker 110 with a resolution of about 0.1 mm, although a more or less precise resolution is possible and may be suitable depending on the particular application. The probe 150 may further be configured to detect markers 110 within a range of up to 12 inches or more.

In one embodiment, the tip sensor pair 151 is positioned in the sensing tip 164 of the probe 150 and the base sensor pair is positioned outside of the range 153 of the tip sensing pair 151. In one embodiment, the distance to the marker 110 may be determined by taking the difference of the magnetic field measured by the tip sensor pair and the magnetic field measured by the base sensor pair. This difference represents the magnetic field strength of the marker 110 and is proportional to a distance of the probe 150 the marker 110. The accelerometer data from either the tip sensor pair or base sensor pair may then be used to determine the orientation of the probe 150 itself and the direction to the marker 110. This process, only briefly summarized here, will be presented in greater detail below.

In some embodiments, analysis and determination of the distance and direction to the magnetic marker 110 may be executed by the probe 150 itself, for example, in a microprocessor. In some embodiments, the data obtained from the probe 150 (e.g., the sensing and base sensor pairs) may be relayed to an external device 170 and analyzed there. The distance and direction to the marker 110 may be displayed on the probe 150 itself and/or a display 171 of the external device 170. The external device 170 may be a computer, tablet, smartphone, or similar device. The external device may include a display 171 and one or more inputs 173, such as a keyboard, mouse, touchscreen, or the like. In some embodiments, the probe 150 can be used as an input device for the external device. For example, by selecting an appropriate input button 154 on the probe 150, the probe may operate as a 3D mouse for manipulating content on the display 171 of the external device. The external device 170 may further include one or more processors, memories, or storage devices. In the system 100, the probe 150 and the external device 170 may be connected via a link 181 so as to communicate with each other. The link 181 may be wired or wireless, for example through a Bluetooth or Wi-Fi connection, and may further be direct, with no intermediate device, or indirect, with communication routed through one or more additional devices. In some embodiments of the system 100, the external device 170 may be omitted.

The system 100 may allow for marking of tumors previously inaccessible to surgeons, such as brain tumors because of the small size of the injection needle that may be used to insert the small micro-magnets and the long range 153 in which the probe 150 can locate marker 110. For example, the range 153 of the probe may be 6 inches or more (for example, the radius of the range 153 is 6 inches or more), such as up to 12 inches or more in some embodiments. This may not be possible with RFID markers due to the size and strength limitations thereof. Other applications of the system 100 include, but are not limited to, locating endotracheal tubes, catheters, magnetic contrast agents, magnetic tumor antibody agents, surgical sponges, and instruments, such as by attaching magnetic markers to these objects.

Example Probe Components and Functions

Figure 2A:
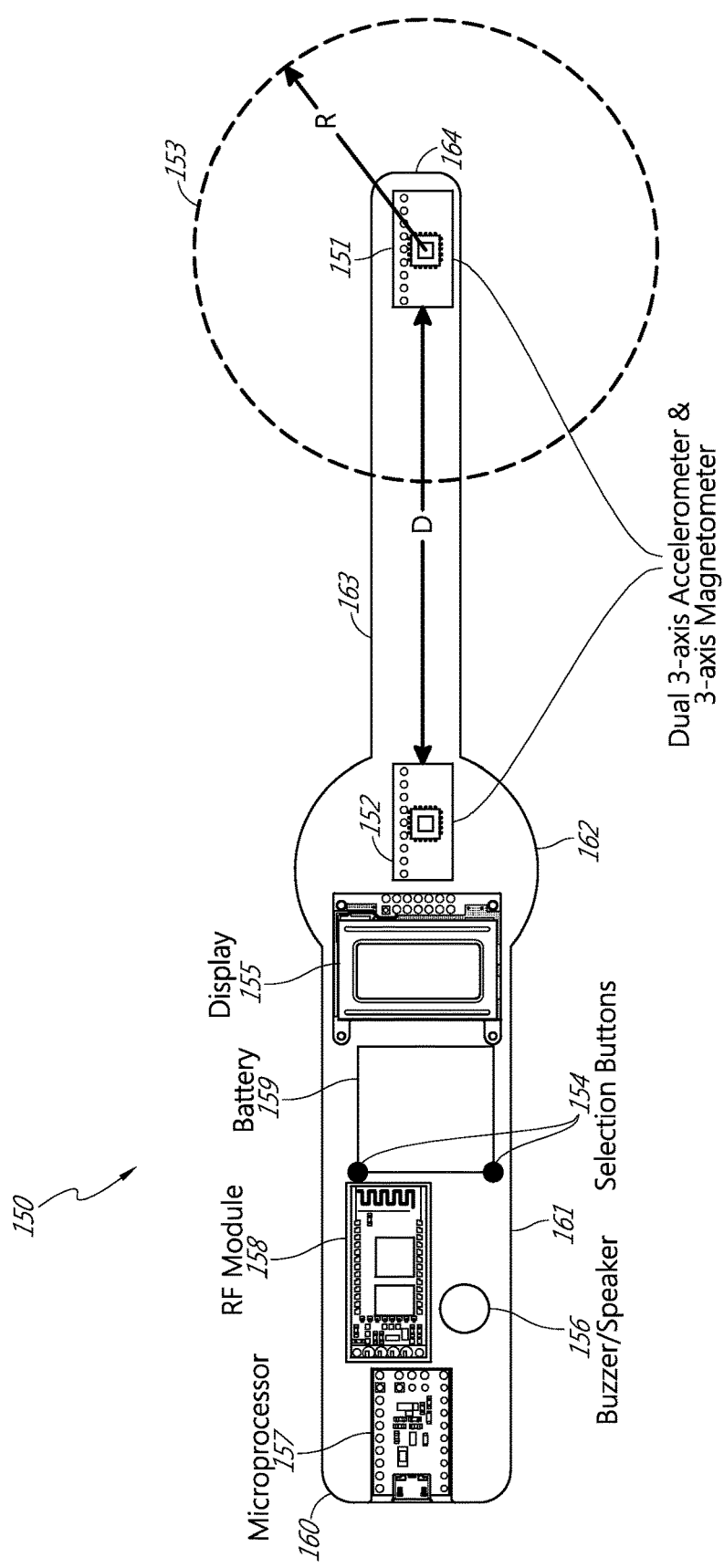
FIG. 2A is a diagram illustrating the handheld probe and example components and the placement thereof, according to one embodiment.

FIG. 2A is a diagram illustrating the handheld probe 150 and example components and the placement thereof, according to one embodiment. The embodiment of FIG. 2A is merely one example of a configuration of the handheld probe 150; the components may be arranged differently in other embodiments without departing from the scope of this disclosure.

In the example of FIG. 2A, the probe 150 includes a housing 160 with the internal components of the probe 150 positioned therein. The housing 160 may be formed of plastic, non-magnetic metal, or other suitable material. In some embodiments, the housing 160 is formed of an easily cleanable material for sterile use in an operating room or other medical environment. In some embodiments, the housing 160 may be removable and/or disposable. In the example, the housing 160 is configured in size and shape to include a base 161, a protruding portion 162, and an extension portion 163 as shown. A majority of the internal components of the probe 150 may be located within the base 161 and/or the protruding portion 162. In some embodiments, the base 161 is configured as a handle, which may allow a user to hold the probe 150 in a wand-like manner. In some embodiments, the protruding portion 162 may be configured as a grip, which can allow a user to hold the probe 150 in the same orientation as one would hold a pencil. For example, the protruding portion 162 may be configured with a generally spherical shape that fits into a user's palm to provide stability to the probe 150 during use. In some embodiments, the protruding portion 162 is not configured as a grip. This may allow the base sensor pair 152 to remain out in the open when positioned within the protruding portion 162. The housing 160 may also include an extension portion 163 that extends generally away from the base 161 and protruding portion 162 toward the sensing tip 164 of the probe 150. In some embodiments, the user may hold the extension portion 163 during use. In some embodiments, the probe may not include a protruding portion 162. In some embodiments, the housing 160 of the probe 150 may comprise a constant cross-sectional shape along its length. For example, in some embodiments, the housing 160 of the probe 150 is configured as cylindrical wand with a constant circular cross-section along its length.

In some embodiments, the housing 160 may have an overall length of approximately 220 mm, an overall width of approximately 25 mm, and an overall height of approximately 15 mm, although these dimensions are provided as examples only, and the size of the housing is not intended to be limited thereto.

In this example, the internal components of the probe 150 include a tip sensor pair 151, a base sensor pair 152, one or more input buttons 154, a display 155, a buzzer or speaker 156, a microprocessor 157, an RF (wireless) module 158, and a battery 159. In other embodiments, a probe may include any portion of these components and/or additional components.

As used herein, the terms "accelerometer-magnetometer" or "sensor pair" may refer to a dual three-axis accelerometer and three-axis magnetometer paired together on a single chip or on separate chips adjacent one another. For example, each accelerometer-magnetometer or sensor pair may be a LSM303D available from STMicroelectronics of Geneva, Switzerland. The product sheet for this accelerometer-magnetometer is available at http://www.st.com/st-web-ui/static/active/en/resource/technical/document/datasheet/DM00057547.pdf, and is hereby incorporated by reference in its entirety. A combination magnetometer-accelerometer pair, packaged in a single chip may be preferred in some embodiments of the probe 150 as it will tend to reduce the distance and placement error between the individual magnetometer and accelerometer sensors. However, this is not required in all embodiments of the probe 150 and discrete accelerometers and magnetometers may be used. As noted above, a sensor pair includes a magnetometer sensor and an accelerometer sensor. A magnetometer sensor measures magnetic field strength and typically provides a three component data output representing the three-orthogonal components of the magnetic field (itself a vector, with direction and magnitude). An accelerometer sensor measures not only the acceleration of the sensor, but also the sensor's orientation to earth's gravity. The accelerometer typically similarly provides a three component data output representing the acceleration of the sensor. FIGS. 3A and 3B and the accompanying description provide additional information about the axes and function of the accelerometer-magnetometers.

In the example of FIG. 2A, the tip sensor pair 151 is positioned at the sensing tip 164 or end of the extension portion 163 and separated from the base sensor pair 152 by a distance D, and the base sensor pair 152 is positioned within the base 161. In some embodiments, the base sensor pair 152 may be positioned in the base 161, the protruding portion 162, and/or the extension portion 163. In some embodiments, the base sensor pair 152 is positioned within the protruding portion 162 so as to not be covered by a user's hand when the probe 150 is held. In the illustrated embodiment, each of the sensor pairs 151 and 152 have a range 153 within which they can sense the magnetic field of a marker 110. The range 153 is generally spherical and centered on the sensor pair. The size of the spherical range is represented by a radius R. Notably, in FIG. 2A only the range 153 of the tip sensor pair 151 is shown, although the base sensor pair 152 has a similar range centered on itself. The range 153 is a factor of the sensitivity of the sensor pair as well as the strength of the magnetic field of the marker 110. For example, a marker 110 with a stronger magnetic field (e.g., a larger magnet) can be sensed at a greater radius R from the tip sensor pair 151.

In one embodiment, the distance D between the tip sensor pair 151 and the base sensor pair 152 may be configured to be at least twice the radius R. This configuration reduces the likelihood of a marker 110 being sensed by both the tip sensor pair 151 and the base sensor pair 152. However, this need not be the case in all embodiments. In another embodiment, the distance D is at least as large as the radius R. In some embodiments, the distance D may be approximately 500 mm to approximately 50 mm or less. In some embodiments the radius R may be approximately 250 mm to 1 mm. These ranges are provided only by way of example, and are not intended to be limiting of this disclosure. In some embodiments, as the radius R of the range 153 is decreased, the resolution or precision of the probe 150 increases because the incremental scale of the magnetometer in a sensor pair is divided over a shorter distance. For example, the LSM303D chip referenced above outputs raw magnetometer data on a 16-bit binary scale. When the radius R of range 153 is divided into the chips binary scale, a shorter radius R produces a higher resolution because each bit represents a smaller incremental distance.

In one embodiment, the tip sensor pair 151 and the base sensor pair 152 are aligned with each other so that the three-axes (as shown in FIGS. 3A and 3B) of each are also aligned. That is, the x-axis of the tip sensor pair 151 and the x-axis of the base sensor pair 152 are configured to be parallel; the y-axis of the tip sensor pair 151 and the y-axis of the base sensor pair 152 are configured to be parallel; and the z-axis of the tip sensor pair 151 and the z-axis of the base sensor pair 152 are configured to be parallel. This configuration may produce increased accuracy in the results and simplify the computations involved in determining the location of the marker 110. Further, in one embodiment, the tip sensor pair 151 and the base sensor pair 152 are aligned along a central longitudinal axis of the probe 150.

The tip sensor pair 151 and the base sensor pair 152 are each electrically connected to the microprocessor 157, such that the microprocessor 157 receives the data output from each. The microprocessor 157 may be a ATmega16U4/ATmega32U4 available from Atmel. The data sheet for this microprocessor is available at http://www.atmel.com/Images/Atmel-7766-8-bit-AVR-ATmega16U4-32U4_Datasheet.pdf and incorporated herein by reference. Other microprocessors may be used. In general, the microprocessor 157 analyzes the output data from the tip sensor pair 151 and the base sensor pair 152 to determine the distance and direction to the marker 110. Accordingly, the microprocessor 157 may be configured with instructions for making this determination. The process by which the microprocessor 157 determines the distance and direction to the magnetic marker 110 will be described in greater detail below. In some embodiments, the probe 150 may include more than one microprocessor 157.

In the example of FIG. 2A, a display 155 is electrically connected to the microprocessor 157. The display 155 extends through a window in the housing 160 such that it is viewable by the user. The display 155 may provide information to the user regarding the distance and direction to the marker 110 as determined by the microprocessor. In some embodiments, the display 155 provides information regarding the position of the marker 110 to the user in text, for example: "Distance: 10.5 mm." In some embodiments, the display 155 provides a graphical representation of the information. For example, the display may include an arrow that points towards the marker 110. The arrow may update in real time as the user moves the probe 150 relative to the marker. The display 155 may provide a combination of textual and graphical information to the user. The display 155 may also provide additional information to the user. For example, as will be described below, a balancing process may be performed with the probe 150 before use, and the display 155 may provide the user information regarding the balancing. Further, the display 155 may allow a user to access various menus and settings for using the probe 150, for example, volume settings, battery information, and/or magnetic field strength range adjustment settings that may be used increase sensitivity as the measured distance decreases, among others. Input buttons 154 may be included for navigating the menus, and may include, for example, a "select" button and a "next" button. However, the probe 150 may be modified to include other input and selection methods. For example, the probe 150 may include a touchscreen, or input can be entered through the external device 170. In some embodiments, the display 155 and/or the input buttons 154 may be omitted.

In the example of FIG. 2A, an RF (wireless) module 158 is included in the probe 150 and connected to the microprocessor 157. In some embodiments, the RF module 158 is a Bluetooth module or a Wi-Fi module. The RF module 158 may allow a wireless connection to the external device 170 or another wireless enabled device. In some embodiments, the RF module 158 may be omitted, and the probe 150 may not connect to any other device. In some embodiments, the probe 150 connects to another device via a wired connection. For example, the probe 150 may include a USB port that may be used to connect the probe 150 to the external device 170 via a USB cable.

In the illustrated embodiment, the probe 150 includes a buzzer or speaker 156 connected to the microprocessor 157. The buzzer or speaker 156 provides another mechanism by which the probe 150 can communicate information regarding the location of the marker 110 to the user. For example, the microprocessor 157 may be configured with instructions that cause the speaker 156 to emit a tone indicative of the position of the marker 110 relative to the probe 150. In one embodiment, the frequency (pitch) of the tone may indicate the distance to the marker 110 and a warble (or small undulation in the frequency) in the tone may indicate the orientation of the probe 150 relative to the marker 110. For example, a user may move the probe 150 relative to the patient's body 101 while listening to the tone emitted by the speaker 156. As the frequency of the tone increases, for example, the user will understand the probe is being moved closer to the marker 110. The user may also adjust the orientation of the probe 150 so as to remove the warble from the tone. When the user finds a probe orientation that removes the warble from the tone, this indicates that the probe 150 is pointed at the marker 110. Other audible methods for communicating the location of the marker 110 are possible. Moreover, the buzzer or speaker 156 may be configured to vibrate to provide a haptic feedback to the user regarding the position of the marker 110. In some embodiments, the buzzer or speaker 156 may be omitted.

In the example, a battery 159 is included to power the components of the probe 150. In some embodiments the battery may be rechargeable, and the probe 150 may include a recharging port. In some embodiments, the battery 159 may be omitted, and the probe 150 may include a wired connection to a power source. For example, the probe 150 may be powered via USB connection to the external device 170.

In some embodiments, the internal components of the probe 150 may be assembled onto a single printed circuit board (PCB) that is configured to fit within the housing 160. However, in other embodiments the components may be separate or assembled onto more than one PCBs.

While many embodiments of the probe 150 are described herein as including two sensor pairs (each including a magnetometer and accelerometer), in some embodiments the probe 150 includes only a single accelerometer along with two magnetometers (spaced in the same manners as discussed herein with reference to spacing of the sensing and tip sensor pairs). For example, in one embodiment the probe 150 may include base sensor pair 152 (having a magnetometer and accelerometer as discussed herein) and only a magnetometer (without an associated accelerometer) near the sensing tip 164 of the probe 150; or alternatively may include tip sensor pair 151 (having a magnetometer and accelerometer as discussed herein) and only a magnetometer (without an associated accelerometer) in the base 161 of the probe 150. In another embodiment, the probe 150 may include magnetometers at each of the sensing tip 164 and base 161 of the probe (e.g., spaced in a similar manner as discussed herein with reference to spacing of base and tip sensor pairs) and a single accelerometer (e.g., on a separate chip) placed at any location within the probe 150. In some embodiments, the probe 150 may not include an accelerometer and instead include a base and tip magnetometer and provide the functionality and features associated with the magnetometers. Any probe embodiments disclosed herein may be adjusted to include any of these different combinations of accelerometer and/or magnetometer sensors. Such adjustments to the use of magnetometer sensor pairs are applicable to the removable and/or disposable sensing tips also, such as those discussed with reference to FIGS. 2C and 2D. For example, in one embodiment a removable sensing tip may include two magnetometers (spaced within the sensing tip) and an accelerometer may be included in the probe base 161 (to which the sensing tip is removably attachable) so that the sensing tip size may be further reduced since an accelerometer is not included in the sensing tip.

Figure 2B:
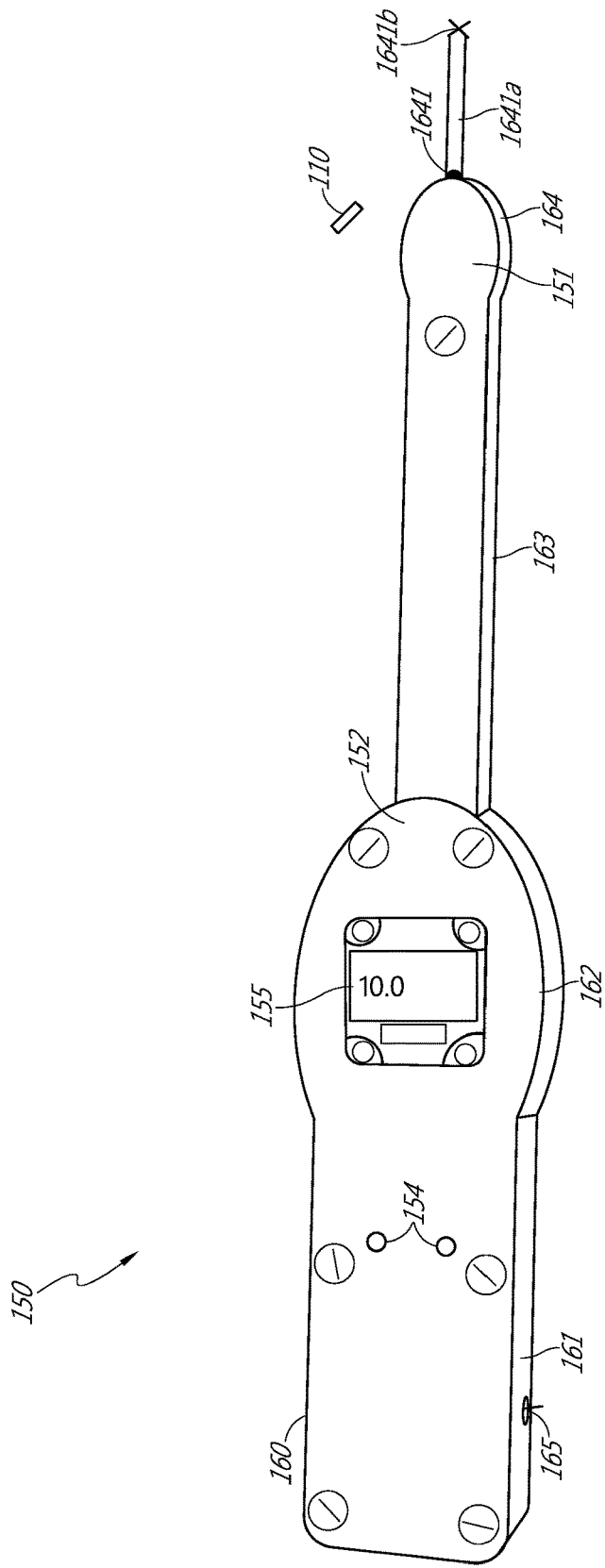
FIGS. 2B through 2D illustrate additional example embodiments of a handheld probe.
Figure 2C:
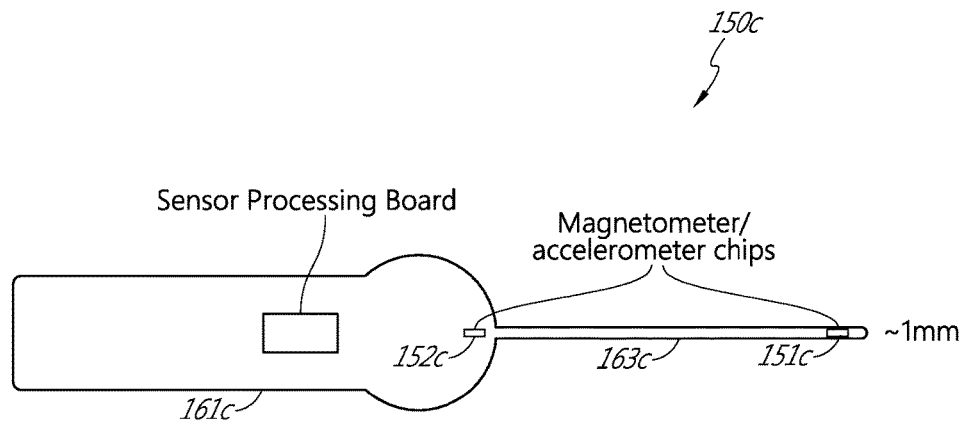
Figure 2D:
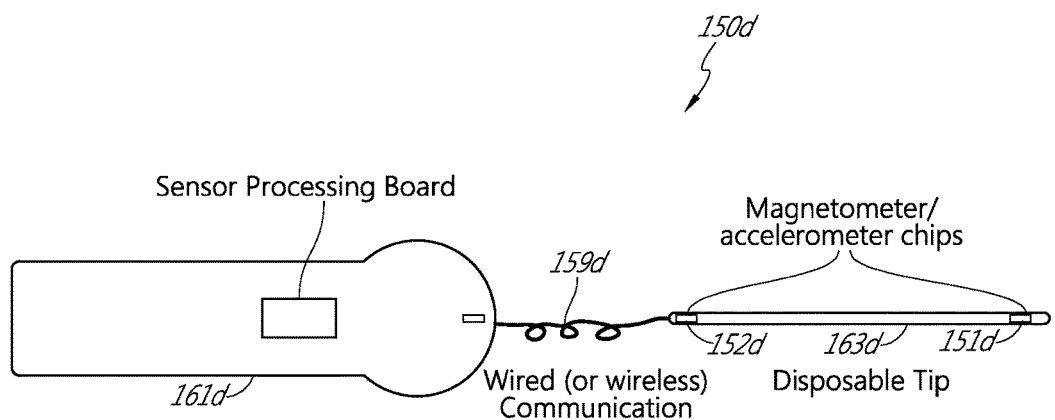

FIGS. 2B through 2D illustrate additional embodiments of a handheld probe. FIG. 2B shows an embodiment of the probe 150 with the housing 160 closed, encapsulating the internal components. The input buttons 154, the display 155, and an on/off switch 165 extend through the housing for access by the user. The housing 160 includes the base 161, the protruding portion 162, and the extension portion 163. The sensing tip 164 is configured as a nub and accommodates the tip sensor pair 151. The base sensor pair 152 is positioned within the protruding portion 162. In the example of FIG. 2B, the probe 150 includes a laser pointer 1641 positioned at the sensing tip 164. The laser pointer 1641 is aligned with the longitudinal axis of the probe 150 so as to point in substantially the same direction as the probe 150 itself. The light beam 1641a emitted by the laser pointer 1641 provides a visual illustration of the location 1641b at which the probe 150 is pointed.

FIG. 2C shows an example of a probe 150c, wherein the extension portion 163c (or sensing member 163c) comprises a narrower member that may be insertable into tissue, such as into an incision in tissue. In one embodiment, the sensing member 163c is sized and comprised of materials the same as or similar to a surgical needle. In these embodiments, the sensing member 163c may be made from a non-magnetic material. For example, the sensing member 163 may be made from a polyether ether ketone (PEEK) material, among others. The Sensor Processing Board illustrated in FIGS. 2C and 2D may include the same or similar microprocessor 157 as discussed herein and may execute similar software or firmware. Additionally, although not illustrated, the probes of FIGS. 2C and 2D (as well as other probes discussed herein) may include some or all of the other components of the probe 150 of FIG. 2A as well as any other components and/or functionalities discussed herein.

Depending on the implementation (e.g., the sensing member size) and ongoing development of sensors of smaller sizes, the sensor pairs may be of varying sizes. For example, in one embodiment each sensor pair is 3 mm×3 mm×1 mm (plus a circuit board thickness) in size. In other embodiments, the sensor pairs may be larger or smaller. For example, each sensor pair may be sized to fit within a sensing member having a diameter that is approximately 1 mm or less. The tip sensor pair 151c is positioned at the distal end of the sensing member 163c that may be inserted into tissue. The base sensor pair 152c can be positioned in the base 161c or in the proximal end of the sensing member 163c opposite the tip sensor pair 151c. In some embodiments, the probe 150c, with the sensing member 163c configured as a needle, is used to probe within the patient's body 101, for example, by inserting the sensing member 163c at least partially into the patient's tissue while gripping the probe base 161c. In the example of FIG. 2C, the probe 150 is configured as a narrower device, wherein the probe tip is a blunt or sharp needle. In one embodiment, the tip of the needle is a fixed distance and location relative to the tip sensor pair, such that the device can calculate and report to the user the proximity of the tip of the needle to the implanted magnet. The benefit is that it is easier to very specifically locate a small lesion with a needle compared to a 1 cm thick blunt probe.

FIG. 2D shows an example of a probe 150d with a removable sensing member 163d. In some embodiments, the removable sensing member 163d may be disposable. The tip sensor pair 151d and the base sensor pair 152d are located in the sensing member 163d and spaced apart as described above. The disposable sensing member 163d may include a wired or wireless connection 159d to the probe base 161d. In some embodiments, the disposable tip 163d includes a plug that is receivable into a socket on the probe base 161d. Advantageously, the embodiment of the probe 150d with a removable and/or disposable sensing member 163d may allow the probe 150d to work with variously configured removable sensing members 163d. For example, the probe base 161d can be coupled to removable sensing members of different sizes and sensitivities, such as sensing members having larger or smaller diameters and different spacings between reference and sensor pairs configured to better detect magnetic markers of varying sizes and/or properties.

In another embodiment, the sensing member 163d may communicate directly to the external device 170, such as a smart phone or tablet. In this embodiment, the external device 170 may include the logic (e.g., hardware, firmware, and/or software) for performing the various functions discussed herein with reference to the microprocessor 157, such as receiving raw data from the two sensor pairs of the sensing member 163d and performing the necessary calculations and processing of the data to balance the sensor pairs and provide measurement information based on the received sensor data. In this embodiment, the removable and/or disposable sensing member 163d may communication wirelessly with the external device 170 (e.g., via a WiFi, RF, or Bluetooth signal) and/or may be wired to the external device 170 (e.g., via a port on the proximal end of the sensing member 163d). Thus, in one embodiment, the user can download an application on a mobile device that communicates wirelessly with the sensing member 163d. In one embodiment, various kits of components, such as a kit including multiple sensing members 163d (perhaps of different sizes and/or sensitivities, or each of a same size sensitivity) could be manufactured/shipped to users so that multiple sensing members 163d are readily available for use. Another kit may include a single base and multiple sensing members.

The components of the various embodiments of the probe 150 discussed herein may be arranged in any other configurations between multiple devices.

Example Balancing of Sensor Pairs

FIGS. 3A and 3B show the three axes for each of the magnetometer and accelerometer, respectively, in a sensor pair. While FIGS. 3A and 3B show the magnetometer and accelerometer separately, in some embodiments of the probe 150 (which includes any of the probes 150, 150a, 150b, 150c, 150d, or other unnumbered probe mentioned herein), the magnetometer and accelerometer are integrated together into an accelerometer-magnetometer pair, for example, as in the tip sensor pair 151 or base sensor pair 152, as discussed above. In those embodiments, the magnetometer and accelerometer substantially occupy the same physical location, and the three axes of each may share a common, or nearly common, origin.

Figure 4:
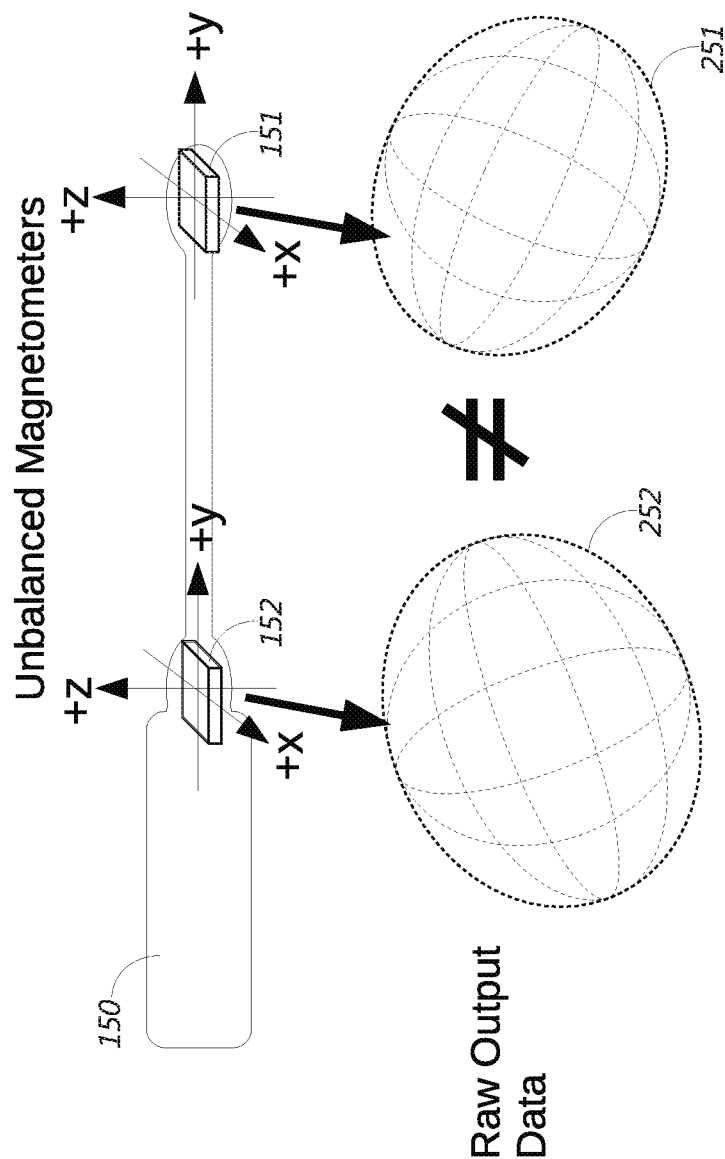
FIG. 4 is a diagram illustrating conceptually the output data from the magnetometer in each of the base sensor pair and the tip sensor pair before the probe is balanced.
Figure 7:
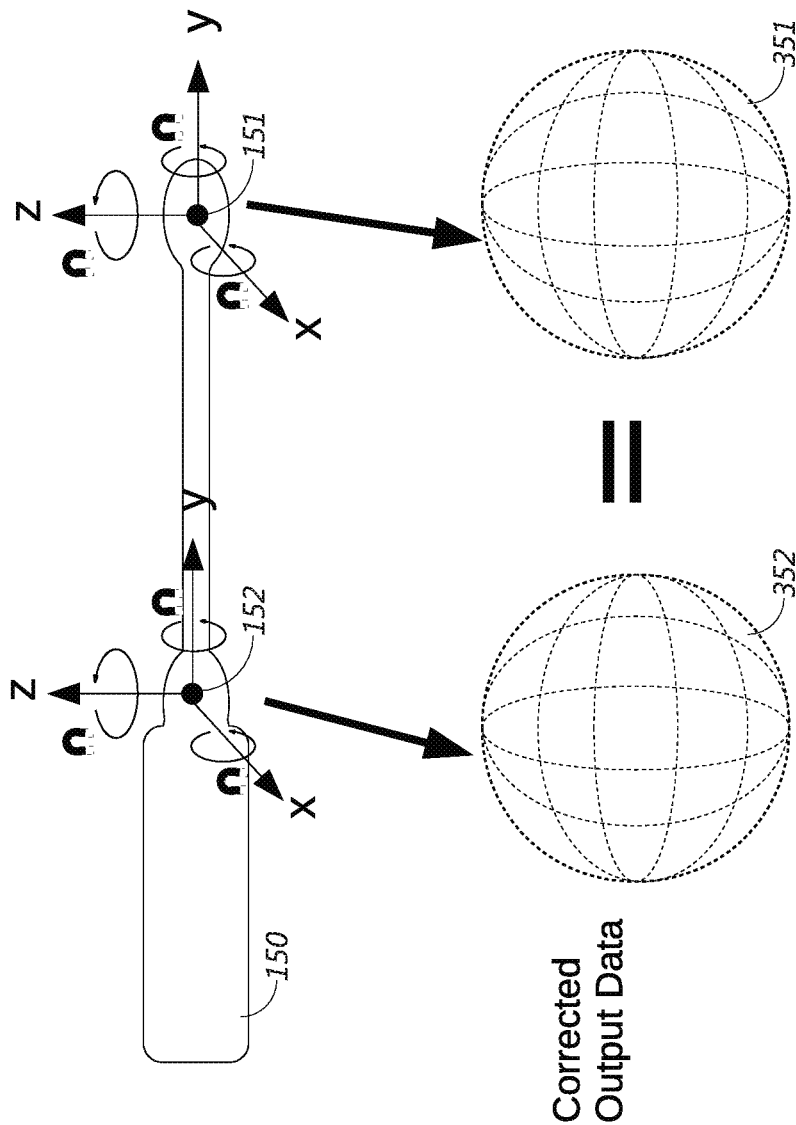
FIG. 7 is a diagram illustrating conceptually the output data from the magnetometer in each of the base sensor pair and the tip sensor pair after the probe is balanced.

FIG. 4 is a diagram illustrating conceptually the output data from the magnetometers in each of the base sensor pair 152 and the tip sensor pair 151 before the probe 150 is balanced. As used herein, the output data may be described as "raw" because, at this stage, it is only a sensor binary number and has not yet been converted into units of Gauss or balanced, as will be described below. In other words, FIG. 4 is representative of the raw output data of the magnetometers of each of the base sensor pair 152 and the tip sensor pair 151 before balancing. This is represented by the two ellipsoids 251 and 252, which correspond to the output data of the magnetometers of the tip sensor pair 151 and the base sensor pair 152, respectively. In an unbalanced state, the size, shape, orientation, and position of the two ellipsoids 251, 252 are likely different. The balancing process, however, determines mathematical transformations that may be applied to the output data of one or both of the magnetometers such that it can be represented by two spheres 351, 352 of equal size (as shown in FIG. 7). An example balancing process is described in detail for a single sensor pair in the following application notes provided by Freescale Semiconductor: "Implementing a Tilt-Compensated eCompass using Accelerometers and Magnetometer Sensors," Doc. No. AN4248, available at http://cache.freescale.com/files/sensors/doc/app_note/AN4248.pdf; "Layout Recommendations for PCBs Using a Magnetometer Sensor," Doc. No. AN4247, available at http://cache.freescale.com/files/sensors/doc/app_note/AN4247.pdf; and "Calibrating an eCompass in the Presence of Hard and Soft-Iron Interference," Doc. No. AN4246, available at http://cache.freescale.com/files/sensors/doc/app_note/AN4246.pdf, all of which are incorporated herein by reference in their entirety.

The ellipsoids 251, 252 in FIG. 4 are representative of the output data of the magnetometers of each of the tip sensor pair 151 and the base sensor pair 152 as the magnetometers are rotated in all directions in a substantially constant magnetic field. The output of a magnetometer comprises three values (for example, x, y, and z values) representing the orthogonal component parts of the magnetic field vector measured by the magnetometer. For a calibrated magnetometer rotating in a constant magnetic field, the x, y, and z output values should fall on the surface of a uniform sphere centered on 0, 0, 0, regardless of the magnetometers orientation (see FIG. 7 and corresponding description). The radius of the sphere 351, 352 will be representative of the strength of the measured magnetic field. However, for an uncalibrated magnetometer, as is shown in FIG. 4, the x, y, and z output values for each magnetometer will trace an ellipsoid 251, 252 as the magnetometer is rotated in a constant magnetic field. The ellipsoid will not likely be centered at 0, 0, 0. Moreover, when magnetometers of the tip sensor pair 151 and the base sensor pair 152 are not balanced, the size and shape of the two ellipsoids 251, 252 will likely be different and, thus, comparison of measurements between the two magnetometers may be inaccurate due to these differences. By using a bases sensor pair 152 and a tip sensor pair 151 and taking the difference of the magnetometer output of each, the probe 150 is able to differentiate the magnetic field of the marker 110 from the general magnetic field in the environment of the probe.

Differences in the output value set for each of the magnetometers may be largely or entirely caused by "hard iron" and "soft iron" interference. "Hard iron" interference is caused by magnetic fields generated by permanently magnetized ferromagnetic components of the probe 150 itself, for example, a permanent magnetic field generated by the buzzer or speaker 156, other components of the probe 150, or other magnetic fields in the area where the probe 150 is used. Because the magnetometers and the other components of the probe 150 are in fixed positions with respect to each other, the hard iron interference manifest itself as an additive magnetic field vector when measured in the magnetometer reference frame. That is, the hard iron interference induces a constant offset in the x, y, and z output data from each magnetometer, regardless of the orientation of the magnetometer. This offset results in the shifting of the ellipsoids 251, 252 discussed above. In some embodiments, the components of the probe 150 which may tend to produce hard iron interference are positioned within the probe housing 160 away from the tip sensor pair 151 and the base sensor pair 152, thus minimizing the hard iron interference.

"Soft iron" interference is caused by the induction of temporary magnetic fields into normally unmagnetized ferromagnetic components of the probe 150, such as the battery 159, by the Earth's geomagnetic field. Soft iron interference therefore depends on the orientation of the probe 150 relative to the Earth's geomagnetic field. Soft iron interference, therefore may add to or subtract from the x, y, and z output of a magnetometer depending on the magnetometer's orientation. This manifests itself in the irregular shape of the ellipsoid 251, 252, as compared with a sphere. In some embodiments, the components of the probe 150 which may tend to produce soft iron interference are positioned within the probe housing 160 away from the tip sensor pair 151 and the base sensor pair 152, thus minimizing the hard iron interference.

Figure 5:
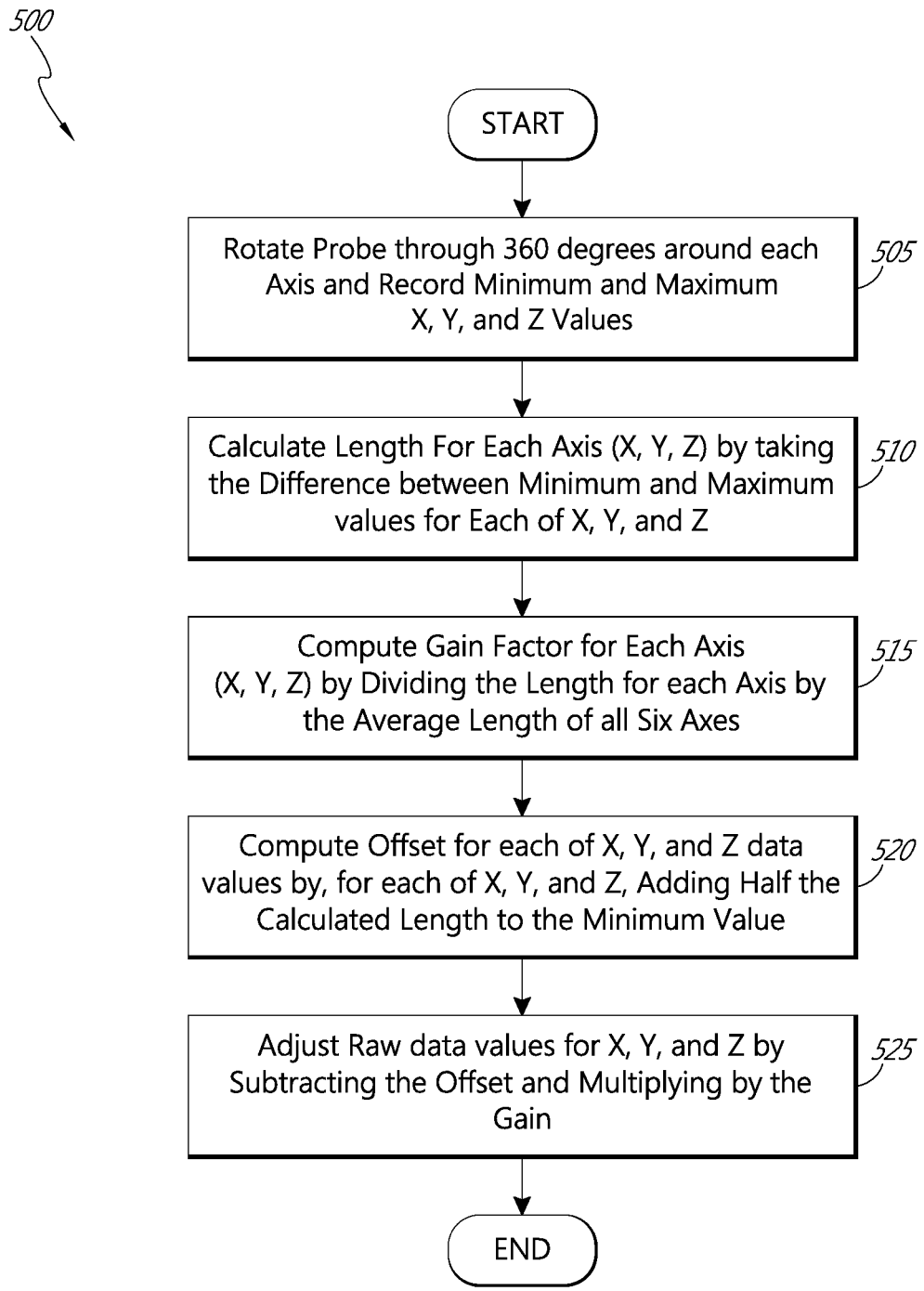
FIG. 5 is a flowchart illustrating an example method for balancing the magnetometers of the tip sensor pair and the base sensor pair of the probe.

FIG. 5 is a flowchart illustrating an example method 500 for balancing the magnetometers of the tip sensor pair 151 and the base sensor pair 152 of the probe 150. FIG. 6A is a table containing sample magnetometer output data that will be used for purposes of providing an example of the method 500 and, similarly, FIG. 6B is a table which presents calculations of a gain and offset that may be used to balance the sensing magnetometer and reference magnetometer that provided the sample data of FIG. 6A. The method of FIG. 5 may be performed by the probe 150 alone and/or in communication with the device 170. Depending on the embodiment, the method of FIG. 5 may include fewer or additional blocks and the blocks may be performed in an order that is different than illustrated.

The method 500 begins with an unbalanced set of magnetometers in a probe 150. In this embodiment, the probe 150 is balanced away from (out of range of) any markers 110. At block 505, the probe 150 is rotated through 360 degrees around each of three orthogonal axes and the minimum and maximum x, y, and z output values are recorded. For example, the probe 150 is rotated 360 degrees in each of the pitch, roll, and yaw directions. As the probe 150 rotates, the magnetometer of each of the tip sensor pair 151 and the base sensor pair 152 outputs a substantially real time stream of x, y, and z values. For each of the tip sensor pair 151 and base sensor pair 152, the maximum and minimum values for each of the x, y, and z values are stored. In some embodiments, the maximum and minimum values are stored in a memory associated with the microprocessor 157, such as a solid state storage device.

For example, in some embodiments, the microprocessor 157 stores the first x output value it receives from the magnetometer of the tip sensor pair 151. The microprocessor 157 then checks each successive x output value against the stored value and replaces the stored value if the successive x value is higher. After one complete rotation of the probe 150, the maximum x value will be stored. This process can be similarly repeated for determining the minimum x value (by checking each successive x value against the stored value and replacing the stored value if the successive value is lower).

In some embodiments, the probe 150 may be rotated through greater than or less than 360 degrees around the three orthogonal axes. In some embodiments, the three axes are not necessarily orthogonal. However, rotating for at least a full 360 degrees around each of the three orthogonal axes will likely increase the accuracy of balancing.

Figure 6C:
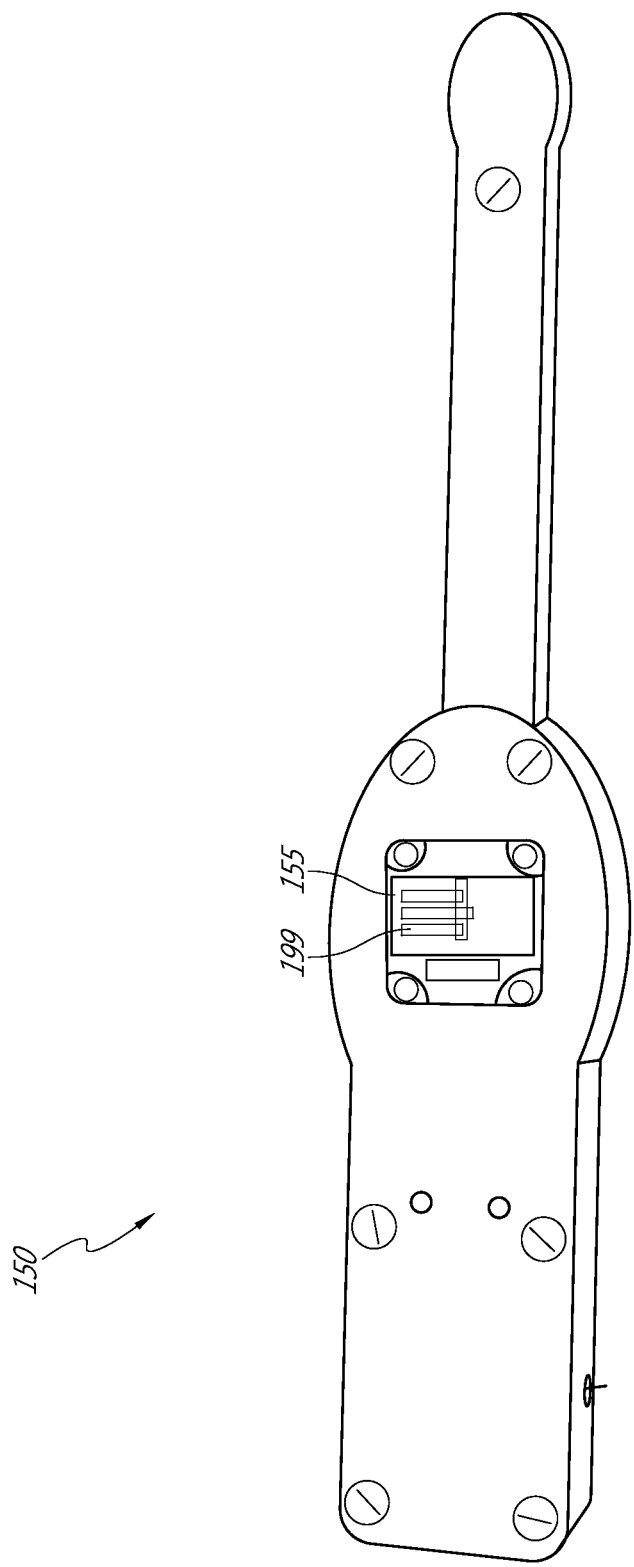
FIG. 6C shows a probe configured to display set of bars that provide visual feedback to the user during the balancing process, according to one embodiment.

FIG. 6C shows a probe 150 configured to display set of bars 199 that provide visual feedback to the user during the balancing process, according to one embodiment. The bars aid the user in successfully balancing the probe 150. For example, the set of bars 199 includes the three individual bars as shown, one bar corresponding to each of the three orthogonal axes around which the probe 150 is rotated during balancing. In the example, as the user rotates the probe 150, each of the three bars 199 is indicative of the real-time calibration of one of the three axes of the probe 150. For example, the bars may indicate a range across an axis, and the result displayed may reflect the constantly changing gain for each axis. In this embodiment, the constantly changing gain may be determined as the maximum value for that axis minus the minimum value for that axis all divided by the average of all the axes. Thus, the bars show the constantly changing gain adjusted values of the magnetometer during balancing because as the probe 150 is rotated the maximum and minimum values for each axis change over the balancing time as higher and lower values are recorded and stored. This, in turn, results in the individual lengths along each axis (e.g., the distance between the maximum and minimum values) also changing over the balancing time and also the average length of all six axes (e.g., the sum of the six individual lengths divided by six) changing over the balancing time. For example, in an implementation where the final gain values after balancing for all axes are 1.00, the bars may display a range of 0.70 to 1.30 with the middle acceptable range box of 1.00±0.02. When the bars display within the middle acceptable range box, the user will know that the probe 150 is balanced. By displaying the data as the three bars the probe 150 does not need to auto-scale the graph range from a minimum to a maximum value for each axis. Accordingly, the probe 150, via the bars 199 on the display 155, is configured to provide feedback to the user during balancing which may aid a user in understanding how to rotate the probe 150. Other methods for providing feedback, for example other visual or audible means, regarding the progress of balancing may be used. For example, in one embodiment an audible alert is provided when the probe 150 has been rotated sufficiently around each axes such that balancing is complete.

Sample minimum and maximum x, y, and z values for each of the tip sensor pair 151 and the base sensor pair 152 are shown in the table of FIG. 6A. The values in the table of FIG. 6A are considered "raw" values because they are unbalanced data received directly from the magnetometers of tip sensor pair 151 and the base sensor pair 152. Conceptually, the maximum and minimum x, y, and z values represent the end points of the three semi-principal axes of the ellipsoids 251, 252 of FIG. 4. In other words, the maximum and minimum values for x, y, and z define the end points of the three orthogonal axes that mathematically define the shape of the ellipsoids 251, 252.

Next, at block 510, the individual length between the maximum and minimum x, y, and z values is determined. This length is representative of the length of the three semi-principal axes of the ellipsoids 251, 252. As shown in FIG. 5, the length is calculated by taking the difference of the maximum and minimum values, or, as shown in FIG. 6B, taking the sum of the absolute values of the maximum and minimum values. The resulting length for each of the x, y, and z directions for the tip sensor pair 151 and the base sensor pair 152 are shown in the "Individual Length" column of FIG. 6B.

At block 515, a gain factor for each of the x, y, and z directions of each sensor pair 151, 152 is calculated by dividing the individual length of each of the x, y and z directions by the average length of the x, y, and z directions. The average length of the x, y, and z directions is calculated by dividing the sum of the individual x, y, and z lengths of both magnetometers by six. The resulting gain factors calculated from the sample data of FIG. 6A are shown in FIG. 6B (in the "Gain" column). Conceptually, the gain factors are scalar quantities that will be used to transform the ellipsoids 251, 252 of FIG. 4 into the spheres 351, 352 of FIG. 7.

At block 520, an offset value is calculated for each of the x, y, and z directions of each sensor pair 151, 152 by adding the average of the maximum and minimum values to the minimum values. Calculated offset values using the sample data of FIG. 6A are shown in FIG. 6B (in the "Offset" column). Conceptually, the offset values represent the shift of the center of the ellipsoids 251, 252 away from center (0, 0, 0) along each of the x, y, and z directions. The offset values are used to translate the ellipsoid 251, 252 back to a common center.

At block 525, the raw output data from the magnetometers of the tip sensor pair 151 and base sensor pair 152 is balanced by subtracting each of the corresponding offset values from the corresponding raw output data and then multiplying by the corresponding gain value.

FIG. 7 is a diagram illustrating conceptually the output data from the magnetometer in each of the base sensor pair 152 and the tip sensor pair 151 after the probe 150 is balanced. As shown in the figure, the range of possible outputs from each can now be represented as equal sized spheres 351, 352. Moreover, each sphere 351, 352 has a common center, such as 0, 0, 0. With the probe 150 correctly balanced, as the probe 150 rotates in a constant magnetic field, the output data from each magnetometer (in x, y, z form) will fall on the surface of the spheres 351, 352. The radius of the spheres 351, 352, which does not depend on direction, is constant and corresponds to the strength of the constant magnetic field acting on the sensor pairs 151, 152. Accordingly, assuming no changes to the constant magnetic field around the probe 150, it is balanced to correctly measure a magnetic field, regardless of the orientation of the probe 150. In some embodiments, the probe 150 may further be configured with a zero adjust function, as discussed below, to account for small variations in the magnetic field around the probe. For example, these variations may be caused by changes in the Earth's geomagnetic field over time. The zero adjust function compensates for subtle soft and hard iron interferences present based on the orientation of the probe that may exist even after balancing. Conceptually, these interferences may be viewed as minor bumps or variations on the spheres 351, 352. The zero adjust function corrects for these bumps.

FIG. 8 is a table containing sample balanced data. The data in the table represents the raw data of FIG. 6A in balanced form. In the first two columns, the minimum and maximum values have been adjusted by subtracting the appropriate offset values. In the last two columns, which contain fully balanced data, the gain factor has been applied. At this point, for each of the base and tip magnetometers, all of the maximum values are equal, all of the minimum values are equal, and the minimum and maximum values are equal in absolute value but have the opposite sign.

Example Magnetic Marker Measurements Using Balanced Sensor Pairs

Figure 9:
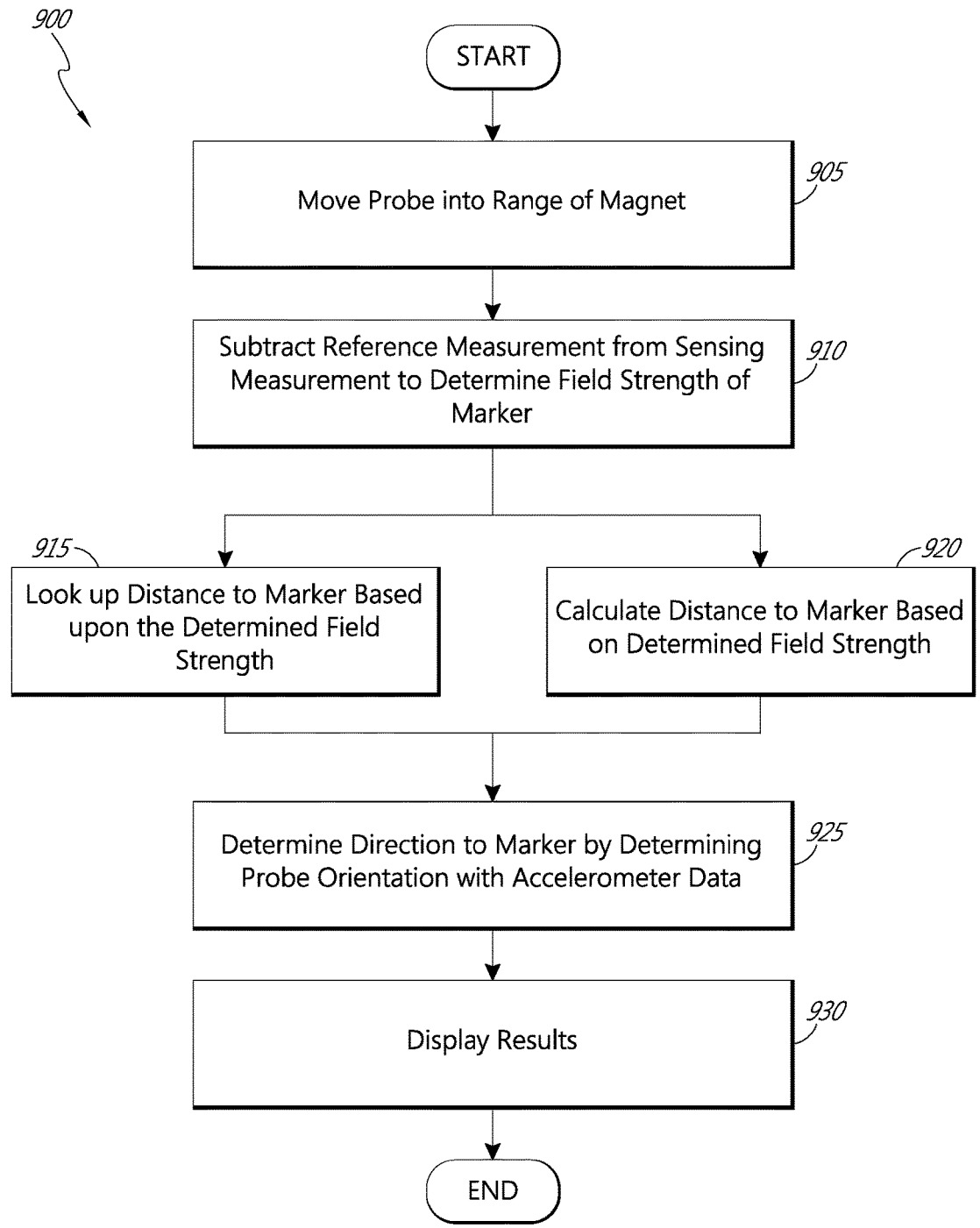
FIG. 9 is an example method for using the probe to determine the three-dimensional location of a marker within a patient's body.

FIG. 9 is a flowchart illustrating an example method 900 for using the probe 150 to determine the three-dimensional location of a marker 110 within a patient's body 101. The method 900 will be discussed in connection with FIGS. 10-13, which include example data for purposes of illustration. Depending on the embodiment, the method of FIG. 9 may include fewer or additional blocks and the blocks may be performed in an order that is different than illustrated.

The method 900 begins with a balanced probe 150 and at least one marker 110 implanted into the tissue of a patient. At block 905, the probe 150, and specifically the tip sensor pair 151, is brought within range of the marker 110 (for example, as illustrated in FIG. 1). This may be done by holding the probe 150 by hand and moving the tip sensor pair 151 over the surface of the patient's body 101 where the marker 110 is believe to be implanted. In some embodiments, the probe 150 contacts the patient's skin. In some embodiments, the probe 150 does not contact the patient's skin. In one embodiment, each of the tip sensor pair 151 and base sensor pair 152 outputs substantially real time accelerometer and magnetometer data to the microprocessor 157.

At block 910, the base sensor pair's 152 magnetometer data is subtracted from the tip sensor pair's 151 magnetometer data. This difference is representative of the magnetic field strength of the marker 110. Block 910 is shown conceptually in FIG. 10.

Figure 10:
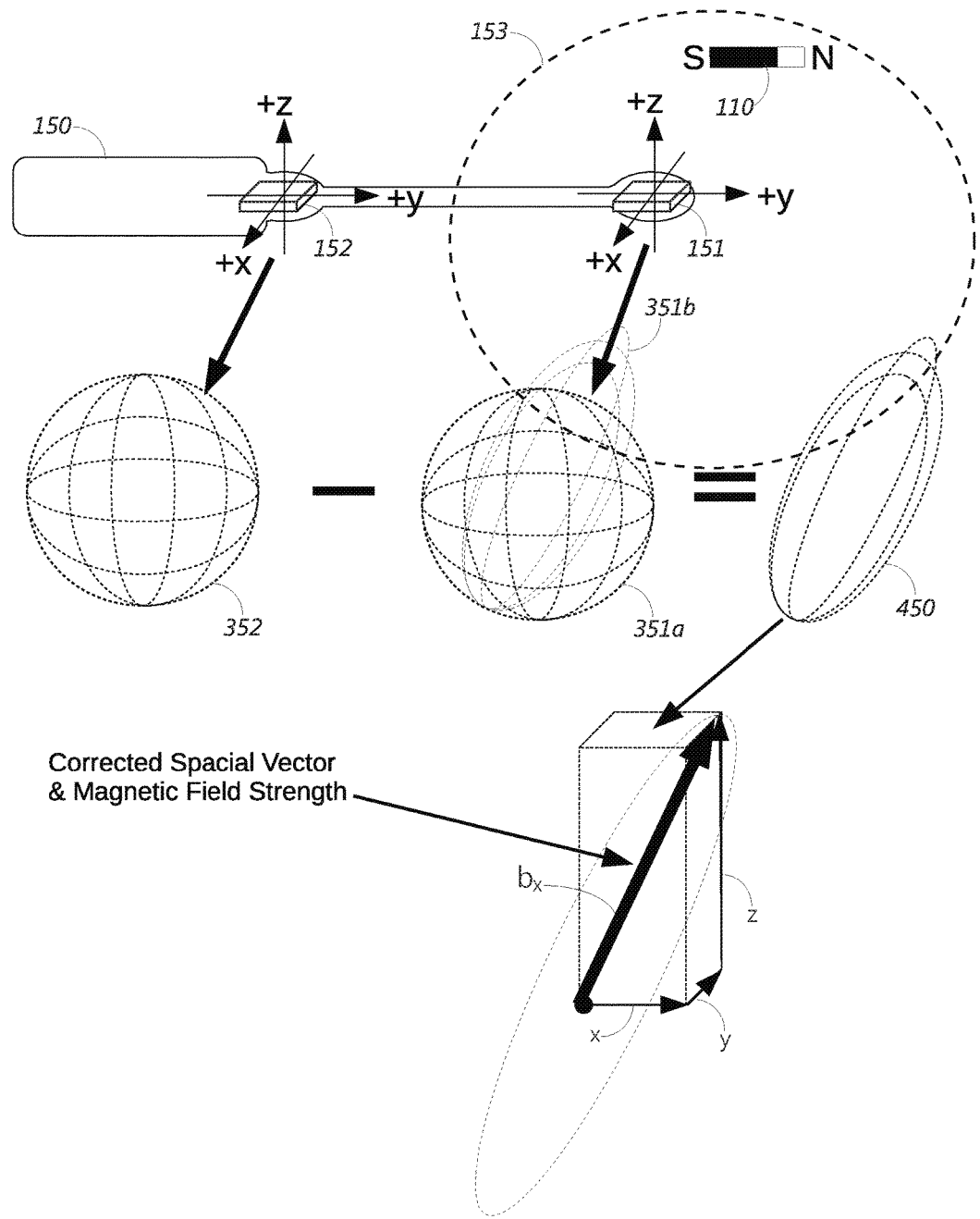
FIG. 10 is a diagram illustrating conceptually determination of the magnetic field strength of a marker with the probe by subtracting the base sensor pair's magnetometer output data from the tip sensor pair's magnetometer output data.

In the example of FIG. 10, the probe 150 has been balanced so that the magnetometer output data of the tip sensor pair 151 and the base sensor pair 152 can be represented as equal sized, concentric spheres 351a, 352. However, because the marker 110 is within the range 153 of the tip sensor pair 151, the magnetic field of the marker 110 is also reflected in the tip sensor pair's magnetometer data output. This component due to the magnetic field of the marker 110 is represented by the shape 351b in FIG. 10. Notably, because the marker 110 is not within range of the base sensor pair 152, its magnetometer data output is not affected by the marker 110. Upon subtraction of the base sensor pair's 152 magnetometer data from the tip sensor pair's 151 magnetometer data, the result is substantially wholly due to the magnetic field of the marker 110. The result is represented conceptually in FIG. 10 by shape 450. Subtracting the base sensor pair 152 data from the tip sensor pair 151 data removes any components that act equally on both base and tip magnetometers, for example, the component due to the Earth's geomagnetic field.

The magnetic field of the marker 110, measured at the tip sensor pair 151 is a vector quantity with length and direction. After taking the difference described above, the probe 150 will have resulting x, y, and z values representing the component parts of that vector. The magnitude of the magnetic field strength $b_x$, then, can be calculated using the Pythagorean Theorem, for example, to calculate a major axis length of the ellipsoid.

FIG. 11 provides tables showing sample data in both raw and balanced form that is representative of raw and balanced data from a probe 150 that is positioned within a measurement range of a magnetic marker. It further illustrates calculation of the magnitude of the magnetic field strength $b_x$ of a marker 110 using that data. The top table presents columns for raw, offset adjusted, and fully balanced (offset and gain adjusted) data for each of the tip sensor pair 151 and base sensor pair 152, for an example marker 110 positioned 17.1 mm from the tip sensor pair 151. As shown, there is a difference in the balanced data between the tip sensor pair 151 and base sensor pair 152. This difference is caused by the magnetic field of the marker 110 acting on the tip sensor pair 151. The differential is calculated with results displayed in the first column, labeled "Differential," of the bottom table (e.g., for the x-axis, by subtracting the "After Gain Corrected" x data for the base sensor pair from the "After Gain Corrected x data from the tip sensor pair).

In some embodiments, the calculated differential represents raw magnetometer output data that needs to be converted into a magnetic field strength value with units of Gauss. For example, the magnetometer raw output data of an LSM303D chip is firmware selectable, and the magnetometer selected allows for different full-scale output sensitivity. The LSM303D allows for selection of ±2/±4/±8/±12 gauss, dynamically selectable magnetic full-scale output over a signed-16 bit number, from −32768 to +32767. The example data presented in FIG. 11 was generated by an LSM303D chip with the ±12 gauss magnetic scale selected. Accordingly, to convert the raw output data to Gauss, the raw output is divided by 32768 and multiplied by 12. Or, in more general terms, the raw output is converted into a magnetic field strength value represented in Gauss by dividing the raw output by the magnetometers scale and multiplying by the Gaussian value represented by each incremental unit of the scale. This is represented in the table of FIG. 11 by the column labeled "Differential/32768*12."

The magnitude $b_x$, of the marker's 110 magnetic field measured at the tip sensor pair 151 may be determined using the Pythagorean Theorem, as shown in the third column of the bottom table of FIG. 11.

In some embodiments, the determined magnitude $b_x$ of the magnetic field of the marker 110 may be adjusted as shown in the column titled "Zero Adjust." The zero adjust is used to compensate for any changes in the magnetic field around the probe, not caused by the marker 110, since the time when the probe 150 was balanced. For example, the Earth's geomagnetic field changes slowly over time. While the balancing process described above calibrates the base sensor pair 152 and the tip sensor pair 151 to account for the Earth's geomagnetic field at the time the probe 150 is balanced, the zero adjust may further compensate for changes in the Earth's geomagnetic field since balancing. The zero adjust may also compensate for other magnetic field changes not caused by the Earth's magnetic field. This zero adjust value modifies the output of the probe 150 due to minor changes in the environment and orientation of the probe. It is not a fixed value, but a user selectable minor offset correction. In the example of FIG. 11, the magnitude of 0.385 Gauss was zero adjusted by a value of −0.076 Gauss for an adjusted Gauss value of 0.309 Gauss. Determination of the zero adjust value is described more fully below in reference to FIG. 14.

Returning to the method 900 of FIG. 9, the distance to the marker 110, as measured from the tip sensor pair 151, can either be retrieved from a lookup table (block 915) or calculated directly (block 920). Both blocks 915 and 920 use the magnitude $b_x$ of the magnetic field of the marker 110 determined at block 910.

At block 915, the distance to the marker 110 is retrieved from a lookup table (an example of which is shown in FIG. 12A) which contains entries relating the magnitude $b_x$ of the magnetic field of the marker 110 to distance. In some embodiments, the lookup table is stored in a memory associated with the microprocessor 157.

The lookup table can be created either experimentally or mathematically. For example, field strength to distance calibration may be performed by placing the micro magnet to be used under the sensing probe tip to record the value of the closest distance or strongest field strength measurement, this will be the first point, then moving the micro magnet to any known measured distance (e.g. 20 mm, 25.4 mm, 50.8 mm) and recording the value as the second point. Since the magnetic field strength falls off roughly exponentially over the distance, multiple calibration points will add to the accuracy.

Another method for calibrating the second point (with a built in reference) is to move the micro magnet along the side of the probe between the sensing probe tip sensor and the reference sensor. Since these two sensors are always at a fix distance in relationship to each other, a lowest field strength differential value displayed will be at the midpoint between these two sensors (where their magnitudes cancel each out), this low point value is at the distance which will always be ½ the distance between the two sensors.

Another method for calibrating the distance to field strength is to use an automated process, including use of the equation below to setup a look-up table for distance verses field strength. For a cylindrical marker 110 with a radius of R and Length L, the magnitude of the magnetic field $B_x$ at the centerline of the marker 110 a distance X from the marker 110 can be calculated with following formula (where $B_r$ is the residual induction of the material):

$$Bx = \frac{Br}{2}\left(\frac{(L+X)}{\sqrt{R^2+(L+X)^2}} - \frac{X}{\sqrt{R^2+X^2}}\right) \quad \text{(Eq. 1)}$$

Using Equation 1, a lookup table can be populated for a marker 110 with a known size (R and L) and a known residual induction ($B_r$). In general the residual induction $B_r$ is a known value which can be obtained from the manufacturer of the magnet. For example, the table can be populated by calculating $B_x$ at incremental distances X. The example lookup table in FIG. 12A has calculated $B_x$ for distances X with a step size of 0.1 mm (e.g., the first column illustrates distances from 0.0 mm to 17.7 mm). Accordingly, by comparing the determined $B_x$ found in block 910 with the corresponding $B_x$ values in the last column of the lookup table of FIG. 12A, the distance X to the marker 110 can be determined within a resolution of 0.1 mm. Depending on the embodiment, the next $B_x$ value that is closest, next highest, or next lowest compared to the calculated $B_x$ from the probe 150 for use in finding a corresponding distance. In other embodiments, distances may be interpolated or scaled based on multiple $B_x$ values included in the lookup table (e.g., the next highest and next lowest values) and their relationships to a measured $B_x$ value.

Alternatively, at block 920 the distance to the marker 110 can be calculated directly by solving Equation 1 for X, given the $B_x$ value determined at block 910. This, however, may be computationally difficult for the microprocessor 157.

Equation 1 is specific to rod shaped magnets; however, similar equations are known in the art for magnets of other shapes, for example, spherical, cuboid, or other three dimensionally shaped magnets. Markers 110 with different shapes may be used by substituting an appropriate and corresponding equation for Equation 1.

FIG. 12B through 12D provides another table of sample data and the calculation of gain and offset values used to balance a probe, according to one embodiment, as well as two example measurements that are calculated with the probe at different distances from a marker.

Example Orientation Determination

A magnetometer sensor will measure the earth's magnetic field to determine North, East, South & West (NESW) orientation when held in the same orientation plane as when it was calibrated. But if the magnetometer sensor moves through pitch, roll or yaw, then heading information calculated for NESW will not be correct. To cancel the effects of the pitch, roll and yaw, an accelerometer is used.

As noted above, an accelerometer (measures acceleration of the sensor) but it also measures the sensors orientation to earth's gravity which at 9.8 m/s² is used to determine UP and DOWN orientation. Thus, one or both of the accelerometers in the base and/or tip sensor pairs may be used at block 925 to determine orientation data of the probe 150.

Figure 13A:
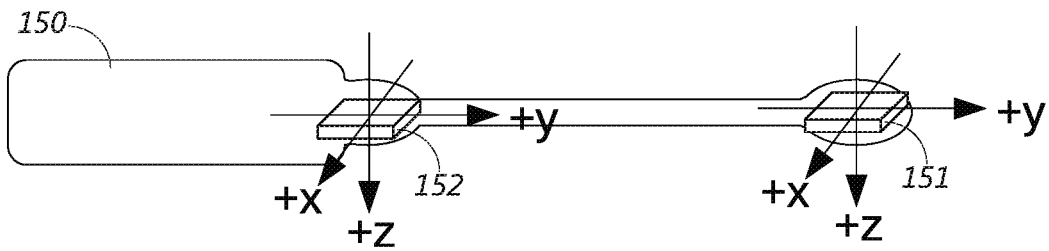
FIG. 13A is a diagram illustrating the use of accelerometer data to determine the orientation of the probe.
Figure 13A:
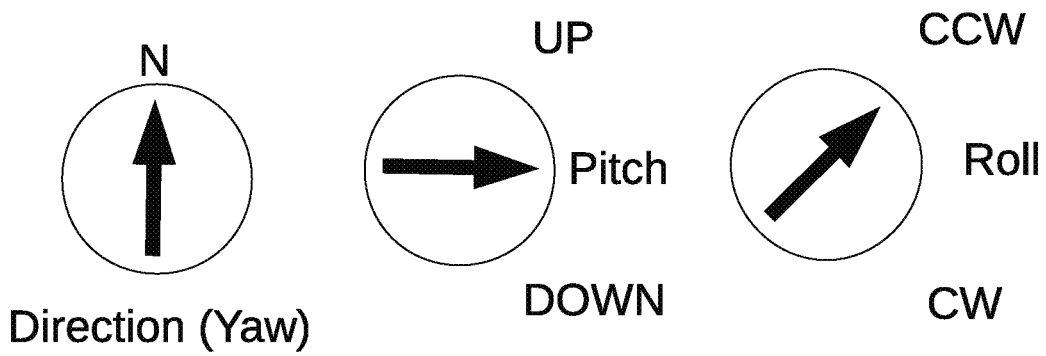

FIG. 13A is a diagram illustrating the use of accelerometer data to determine the orientation of the probe. As previously described, an accelerometer is used to determine the orientation of an object relative to the direction of gravity. Because both the tip sensor pair 151 and the base sensor pair 152 are rigidly attached with reference to one another in the probe 150, the data from the accelerometer of either can be used to calculate the orientation of the probe 150. In the example of FIG. 13A, the orientation of the probe 150 is described in terms of yaw, pitch, and roll. Yaw represents rotation in a horizontal plane relative to North, pitch represents the up or down tilt of the probe 150, and roll represents the rotation of the probe 150 around its longitudinal axis. The three circles in FIG. 13A represent that the probe 150 is pointed north (in the yaw direction), horizontally level (in the pitch direction), and rotated counterclockwise slightly (in the roll direction).

If the probe 150 is not accelerating, both the tip sensor pair 151 and the base sensor pair 152 will output x, y, and z accelerometer data representative of a vector pointing in the direction of gravity. Thus, the accelerometer output provides a determination of an orientation of the probe 150 relative to the direction of gravity. By calculating the yaw, pitch, and roll of the probe 150 (with reference to gravity for a non-accelerating probe 150), the probe 150 can determine the specific orientation of the probe 150 with reference to gravity, which can then be used in to adjust the magnetometer data output to display a direction component output by the probe 150. In one embodiment, the yaw, pitch, and roll of the probe 150 are determined mathematically using the formulas shown in FIG. 13A by taking the arctangent of appropriate rations of the x, y, and z components of the accelerometer data.

At block 930 of FIG. 9, the resulting distance to the marker 110 and probe orientation are displayed. As discussed previously, this may be accomplished in a plurality of ways, including graphically, on a display 155 of the probe 150 or a display 171 of the external device, or audibly, using the speaker 156, among others. In one embodiment, this is done is by first limiting the data to be able to convert a 3D space for display on a 2D screen. For example, when the probe 150 is zero adjusted, the yaw, pitch and roll (See display at 1505 of FIG. 15C) are stored and orientation of the probe 150 is represented at the middle of the 2D display 155 of the probe 150. As the probe 150 is moved from that orientation and the field strength vector is created, the yaw, pitch and roll of the probe 150 are mapped where the peak value is in relation to when it was last zeroed or home in the middle of the display.

Figure 13B:
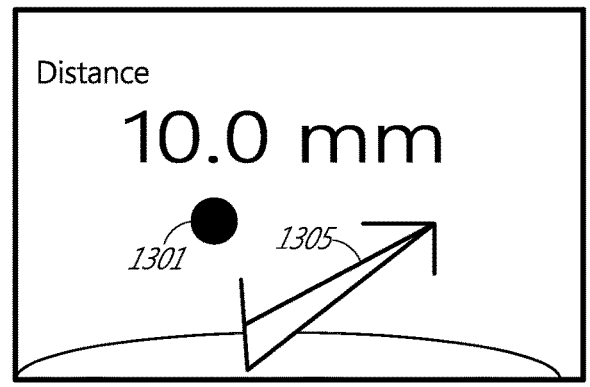
FIG. 13B illustrates three example instances of a graphical representation of the distance and direction from the tip sensor pair of the probe to the marker, according to one embodiment.
Figure 13B:
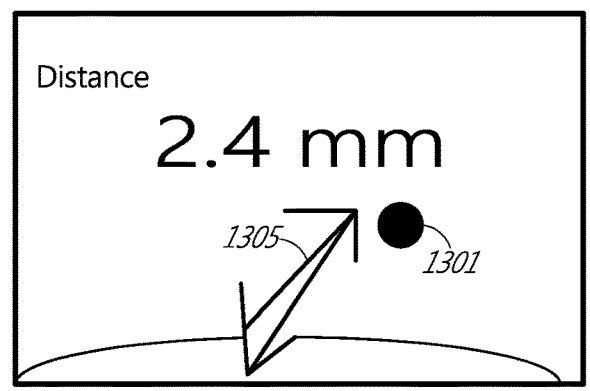
Figure 13B:
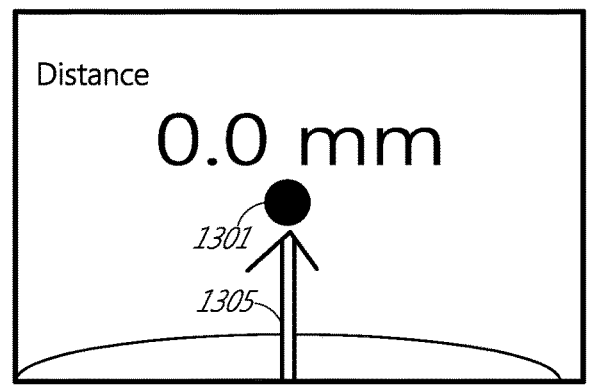

FIG. 13B illustrates three example instances of a graphical representation for displaying the distance and direction from the tip sensor pair 151 of the probe 150 to the marker 110, according to one embodiment. In the examples of FIG. 13B, the dot 1301 represents the location of the marker 110 in relationship to the probe 150 which is represented by the arrow 1305. As the user moves the probe 150, the dot 1301 will move around the display, with the center representing that the marker 110 is straight ahead. The arrow 1305 will change width, length and direction to show the orientation of the probe in the hand. For example, in the first (top) instance the dot 1301 indicates that the marker 110 is to the left of the probe 150 by 10.0 mm and the probe 150 is pointed away from the marker 110. In the first (top) instance, if the dot 1301 stays fixed on the screen and the arrow 1305 appears to swing to the left and touches the dot 1301, so that both are touching at the dot's 1301 left location and display indicates 0.0 mm, the marker 110 is straight in line with the probe 150 but off center from when the probe was zeroed. In the second (middle) instance the dot 1301 is shown to the right of the probe 150, indicated the marker 110 is located to the right of the probe 150 by 2.4 mm, and the probe 150 is pointed generally toward the marker 110. In the third (bottom) instance the dot 1301 is shown in the center of the display, indicating that the marker 110 is straight ahead of the probe 150 at a distance of 0.0 mm. To get to the third instance (bottom) from the first (top) instance, not only was the tip of the probe 150 swung over to the left to meet the marker 110 at 0.0 mm, but the back end of the probe 150 would need to have moved to the left to move the arrow and dot to the center of the display, to match to original direction that the probe 150 was facing when zero adjusted. Thus, these graphics illustrate spatial alignment of the probe 150 independent of its location. These are merely example depictions of a graphical representation of the distance and direction to the marker 110, and other graphical, audible, tactile, and/or other representations of the distance and/or direction are contemplated.

Overview of Balancing and Measuring Processes

Figure 14:
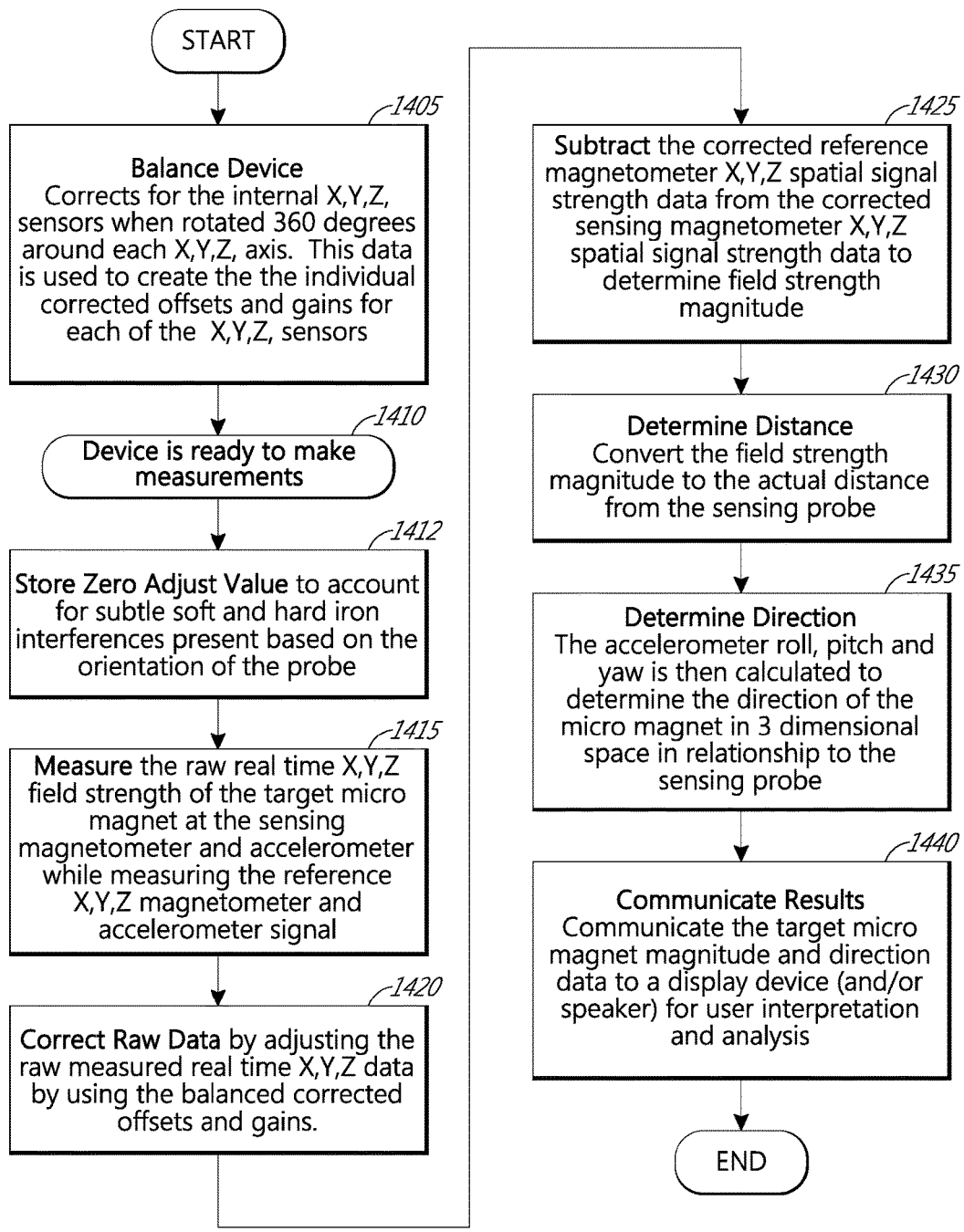
FIG. 14 is a flowchart illustrating operation of the probe 150 including both balancing and measurement, according to one embodiment.

FIG. 14 is a flowchart 1400 illustrating operation of the probe 150 including both balancing and measurement, according to one embodiment. As with the processes above, in some embodiments the process may be performed by the probe 150 alone, or it may be performed by the probe 150 in communication with an external device 170. Depending on the embodiment, the method of FIG. 14 may include fewer or additional blocks and the blocks may be performed in an order that is different than illustrated, In the example of FIG. 14, the probe 150 is initially balanced at block 1405, at which point it is ready to make measurements at block 1410. Block 1412 represents storage of the zero adjust value or values, which are used to account for subtle soft and hard iron interferences present based on the orientation of the probe 150 and changes in the surrounding magnetic field since balancing. In some embodiments, the zero adjust value or values are stored immediately prior to moving the probe 150 into the field of the marker 110. For example, when the zero adjust function is selected, which could be prior to every measurement by the probe, differential x, y, and z values are calculated by subtracting the raw x, y, and z magnetometer output values from the tip sensor pair from raw x, y, and z magnetometer output values from the base sensor pair (e.g., see FIG. 15B). In some embodiments, the zero adjust function will also store the yaw, pitch, and roll values for the probe 150 (e.g., calculated with the formulas of FIG. 13A) to record a location and/or orientation for these differential values. In some embodiments, from that point until the probe 150 is zero adjusted again, these values are used to adjust the offset of the values. During probe balancing, the zero adjust values are all zero.

In one example, when no marker 110 is within the range 153 of the probe 150, and if, for example, the range 153 is 50 mm, the display should indicate that the distance to the marker 110 is greater than 50.0 mm, XX distance, or otherwise indicate that no marker 110 is within range. However, continuing this example, if the probe 150 has not been zero adjusted, the probe 150 may display fluctuating values indicating that a marker is approximately 40-50 mm from the probe 150, even though no marker 110 is within range. This may be because the probe 150 is detecting small changes in the magnetic field that are different than those present at the time or location of balancing. After selecting the zero adjust function, the probe 150 will correctly indicate that no marker 110 is within range.

In some embodiments, the probe 150 includes a manual zero adjust function where the operator can select when to perform the zero adjust function. In some embodiments, the probe 150 may be configured with an automatic zero adjust function, wherein the microprocessor is configured with instructions that execute the zero adjust function based on continuing population of all the points on the balanced spheres 351, 352.

In some embodiments, the zero adjust values can be stored during the balancing of the probe 150, but this would require rotating the probe 150 one hundred and eighty times changing the side movement in one degree increments of orientation on each rotation for a total of 64800 degrees of rotation to cover every possible point on the spheres 351, 352.

At block 1415, real time raw data is received from the accelerometer and magnetometer of each of the tip sensor pair 151 and the base sensor pair 152. At block 1420, the raw data is balanced using the calculated gain and offsets determined at block 1405. At block 1425 the magnetometer readings from the base sensor pair 152 are subtracted from the magnetometer readings from the tip sensor pair 151, and at block 1430 this difference is converted to the actual distance of the marker 110 from the probe 150. At block 1435, the accelerometer data is calculated to determine the orientation and movement of the probe 150.

In some embodiments, the movement of the probe 150 in the magnetic field is used to determine the direction to the marker 110 from the probe. For example, the probe 150 may provide feedback regarding direction in a manner similar to a metal detector. The probe 150 may measure and display the distance to the marker and/or may produce an output tone indicative of the field strength as the probe 150 is moved toward and away from the marker 110. As in metal detecting, the user may move the probe 150 direction feedback in order to mentally determine the direction to the marker 110. As presented above, in reference to FIG. 13B, in some embodiments, this same concept can be implemented graphically. The graphics displayed may not indicate an absolute heading but a graphical representation of the direction in which the magnetic field strength of the marker 110 will be the strongest.

In some embodiments, to get an absolute measured location without any movement of the probe 150 may use at least two magnetometer sensors located at the tip of the probe 150 which then would triangulate the location of the marker 110. For example, with two magnetometers positioned at the tip of the probe 150 and separated by a distance, each magnetometer can be used to calculate respective (and slightly different in most positions) distances to the marker 110 according to the methods described herein. Then, because the distance between the two magnetometers at the tip of the probe 150 is known, the location of the marker 110 can be triangulated.

At block 1440, the resulting location of the marker 110 is communicated to the user. For example, the location data may be provided on the probe itself, or may be sent to an external device 170, such as a smart phone or tablet with a compatible operating system such as Android, Apple OS, or Microsoft Windows. The wireless device can display the location and distance of the probe sensing tip to the micro magnets enabling the surgeon to determine the best path to tumor and tissue marker removal to minimize discomfort and scarring to the patient. As noted above, the probe 150 and/or the wireless device can also have an audio cue as to the distance to the tissue marker and as the probe gets closer the audio pitch can change accordingly so that the surgeon can have both visual and audio feedback as to where to operate on the patient.

Example User Interfaces

Figure 15A:
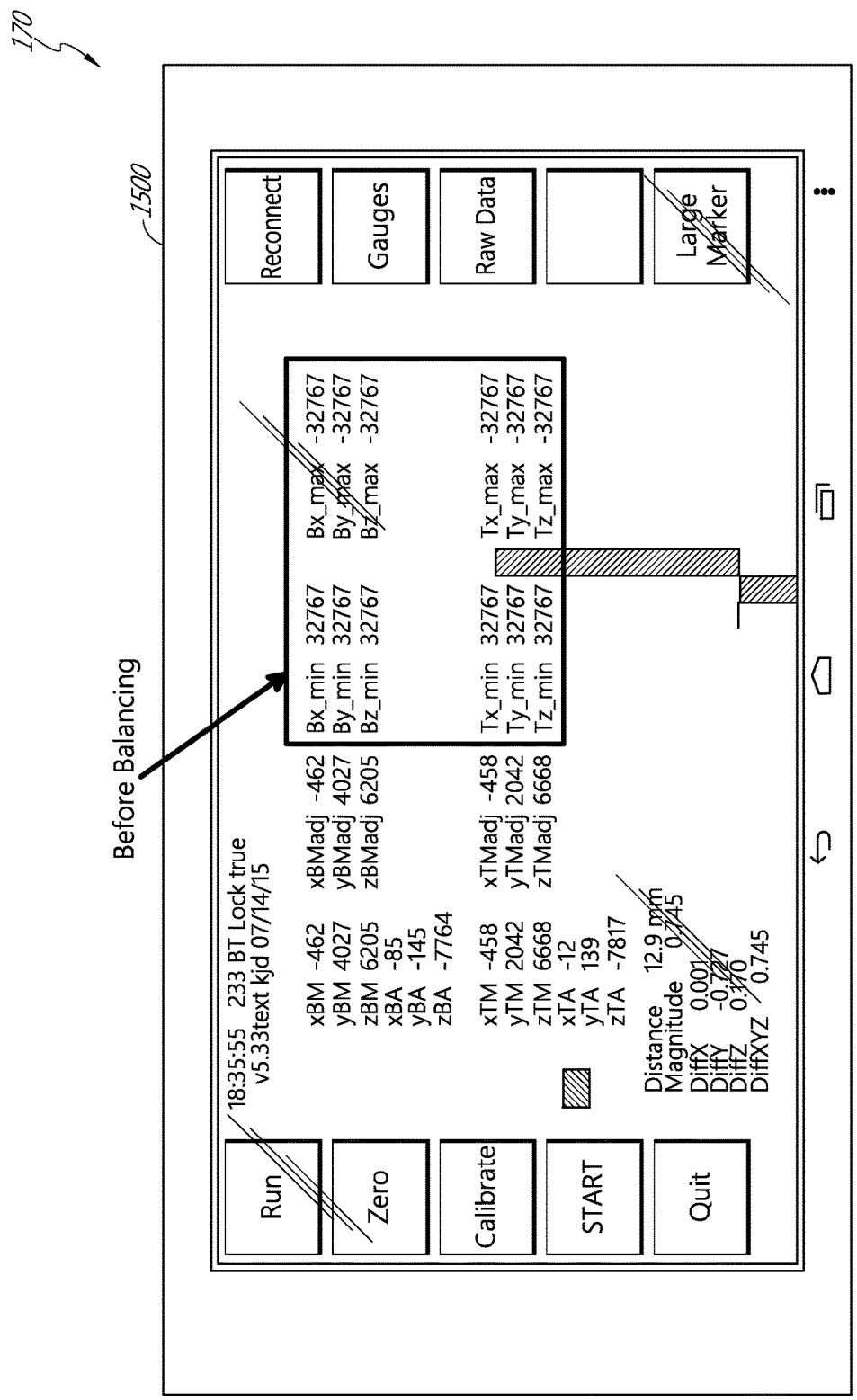
FIGS. 15A through 15C provide examples of a graphical user interface that may be used on an external device in communication with the probe.
Figure 15B:
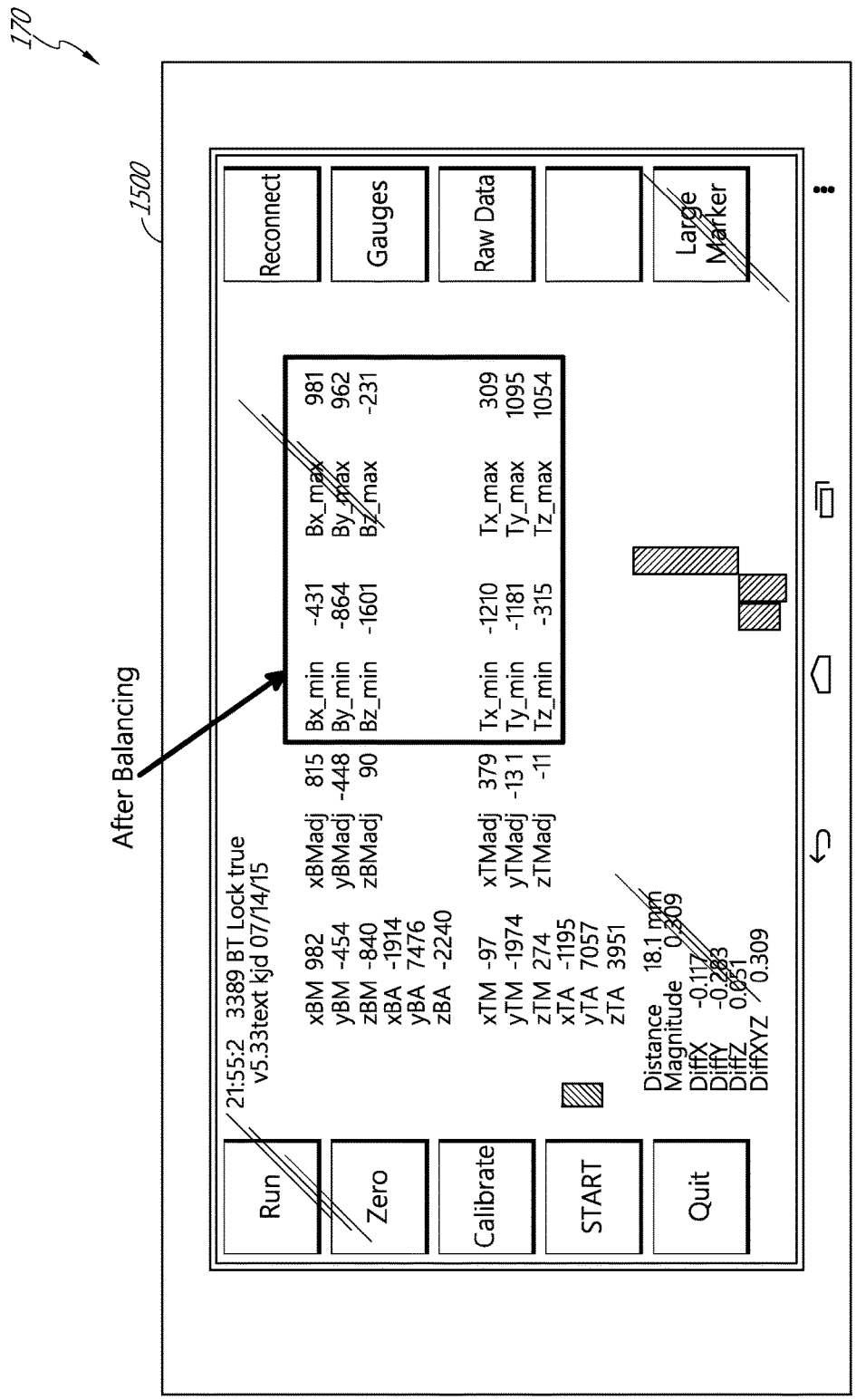
Figure 15C:
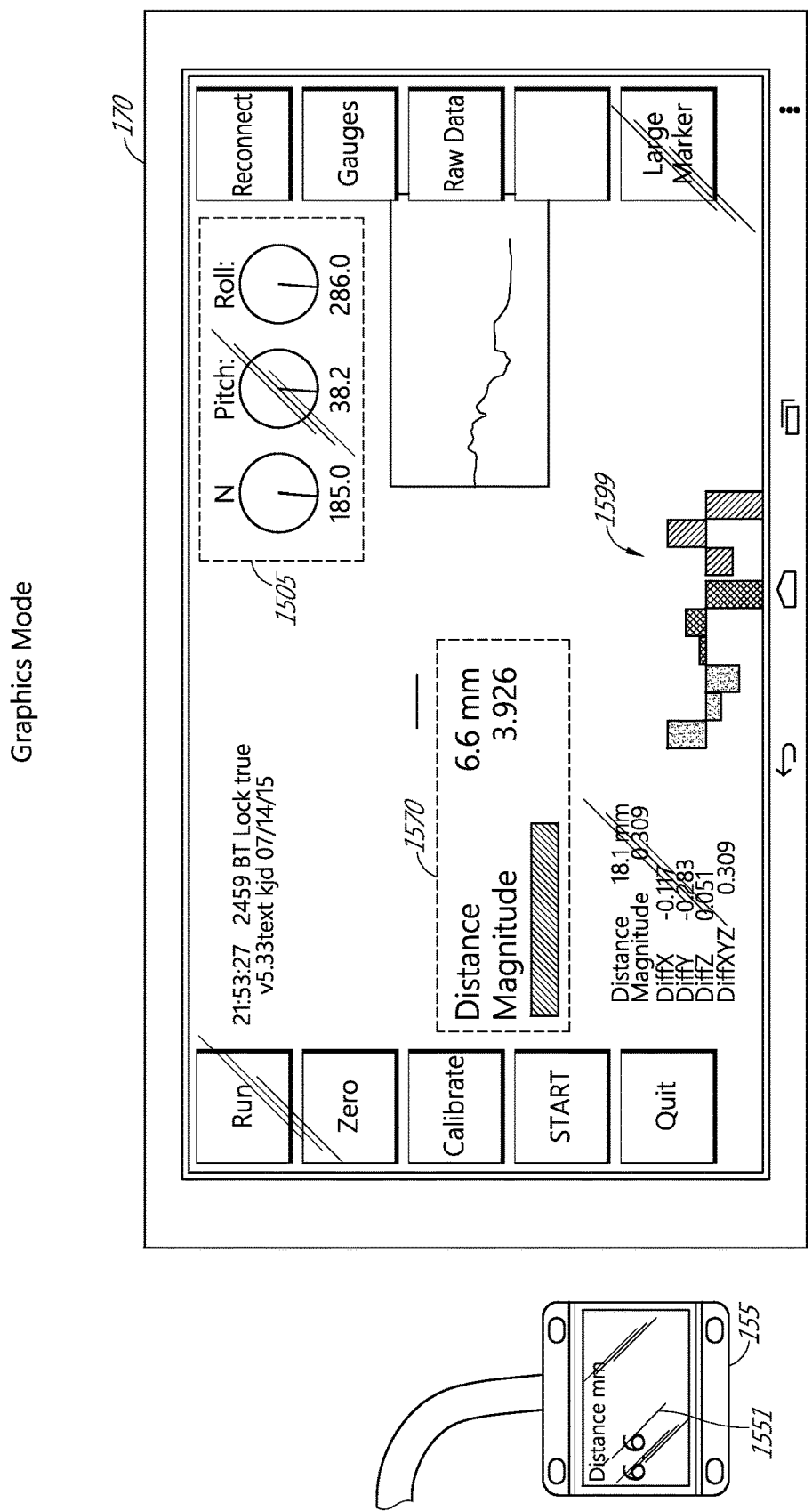

FIGS. 15A through 15C provide examples of a graphical user interface (GUI) 1500 that may be used on an external device 170 in communication with the probe 150, or partially or fully on a display of the probe 150. FIG. 15A is an example of a GUI display before balancing and FIG. 15B is an example of a GUI display after balancing. As shown in the example of FIGS. 15A and 15B, the GUI may allow the user to run, zero, calibrate (e.g., including balancing), start, or quit, as well as options for reconnecting, accessing gauges, and/or viewing raw data. This interface is provided for example only and is not intended to be limiting.

FIG. 15C shows examples of a GUI on an external device 170 and on a display 155 of the probe 150 (although, the display 155 is shown removed from the probe in FIG. 15C). In the example, the display 155 textually relates the measured distance to the marker 110 and graphically indicates the direction to the marker using an arrow 1551. The GUI on the external device 170 textually indicates the distance to the marker in a first portion 1510 and graphically indicates the orientation of the probe 150 in a second portion 1505. The orientation of the probe is shown by providing graphical representation of the yaw, pitch and roll of the probe 150 as described in reference to FIGS. 13A and 13B.

Also shown in FIG. 15C is an example of a graphical indicator 1599 that shows real-time raw data from the magnetometer sensors. In this example, the graphical indicator 1599 includes three sets of colored (shaded) bars. From left to right, the sets of colored bars represent the base sensor pair X, Y, Z value, the tip sensor pair X, Y, Z value and the differential between the two. If the probe 150 is not in a magnetic field of a marker 110, the first two sets of bars (those for the base sensor pair and the tip sensor pair) should appear to be the same height, resulting in the third set of bars having a height of zero (or, possibly not even shown). If the probe 150 is not in a magnetic marker field and the third set of bars (representing the differential between the base sensor pair and the tip sensor pair) are drawn and/or any have a bar height, then the probe 150 should be zero adjusted. After pressing "Zero" button on the display screen or using the selection button on the probe 150 the data will be zero adjusted as described above. If the probe 150 is in a magnetic marker field, the third set of bars will show a differential relative to the corrected differential field strength of the marker, as in shown FIG. 15C. During balancing only the three bars representing the differential represent a relative gain value similar to the bars on the display in FIG. 6C.

Example Uses of Magnetic Markers

In addition to marking potential breast cancer lesions as discussed throughout this disclosure, the system discussed herein may be utilized in a wide number of applications. For example, the system could be used to mark lung nodules, lymph nodes, parathyroid nodules, thyroid nodules, or GI lesions. For example, a gastroenterologist might mark one or more biopsied colonic polyps that are biopsied during a colonoscopy. A pulmonologist might mark one or more lung or bronchial lesions found during a bronchoscopy. A radiologist might mark one or more axillary lymph nodes in a patient with breast cancer. This would facilitate removal of cancerous lesions by a surgeon later.

Even when a lesion is not marked pre-operatively, a surgeon that removes abnormal tissue might mark one or more parts of the surgical specimen in order to direct the pathologist's attention to the proper location. For example, when a mastectomy is performed, a pathologist cannot microscopically examine the entire breast. If a surgeon or radiologist marks the suspicious areas of the specimen based on visual, palpable, or imaging-based guidance, this can facilitate more accurate pathological examination.

Other uses may include locating surgical instruments and sponges used in the operating room and locating magnetic antibody and targeted molecular probes that can attach to cancer cells.

In some embodiments, the probe 150 can be attached to an endoscopic or laparoscopic instrument. In some embodiments, the probe 150 itself may be as simple as a magnet on the tip of a wire or other probe, in which case the system can be used to show the proximity between the magnet at the probe tip relative to an implanted magnet. In that case, the detector could remain external to the patient but would indicate by audio tone or display the relative proximity or location of the probe tip magnet to an implanted magnet. The display could show the relative location of the two or more magnets as the probe is moved (like following the path of a plane vs. a fixed object on a radar screen).

The system also has application outside of the medical field, such as locating pipes that are submerged in the ground, such as irrigation pipes; locating construction materials within walls, such as wall stud locations; and locating various drilling and mining equipment pipes where location relative to the Earth's magnetic field is important. Similar to the medical embodiments discussed above, magnetic markers may be placed in such locations of interest and then located using a probe with both a base sensor pair and a tip sensor pair.

Example Computer Architecture

As noted above, the probe 150 and/or the external device 170 may include various computing components, which may perform some or all of the functions discussed herein. While the probe 150 typically includes fewer components than the external device 170 to maintain a smaller size, it may include any of the components and/or functionalities discussed below with reference to the device 170.

The device 170 may include, for example, a single computing device, a computer server, or a combination of one or more computing devices and/or computer servers. Depending on the embodiment, the components illustrated in the device 170 may be distributed amongst multiple devices, such as via a local area or other network connection. In other embodiments the device 170 may include fewer and/or additional components than are discussed below.

The various devices disclosed herein, including the probe 150 and the external device 170, may be in communication via a network, which may include any combination of communication networks, such as one or more of the Internet, LANs, WANs, MANs, etc., for example.

The device 170 includes one or more central processing units ("CPU"), which may each include one or more conventional or proprietary microprocessor(s). The device 170 may further include one or more memories/storage, such as random access memory ("RAM"), for temporary storage of information, read only memory ("ROM") for permanent storage of information, and/or a mass storage device, such as a hard drive, diskette, or optical media storage device. The memory/storage may store software code, or instructions, for execution by the processor in order to cause the computing device to perform certain operations, such as described herein.

The methods described herein may be executed on the computing devices in response to execution of software instructions or other executable code read from a tangible computer readable medium. A computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

The various illustrative logical blocks, modules, and algorithm steps described in connection with the embodiments disclosed herein, especially those disclosed with reference to the microprocessor 157 and the probe 150 can be implemented as electronic hardware, such as a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. Such processes may be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor.

The exemplary device 170 may include one or more input devices and interfaces, such as a keyboard, trackball, mouse, drawing tablet, joystick, game controller, touchscreen (e.g., capacitive or resistive touchscreen), touchpad, accelerometer, and/or printer, for example. The computing device 170 may also include one or more displays (also referred to herein as a display screen), which may also be one of the I/O devices in the case of a touchscreen, for example. Display devices may include LCD, OLED, or other thin screen display surfaces, a monitor, television, projector, or any other device that visually depicts user interfaces and data to viewers. The device 170 may also include one or more multimedia devices, such as camera, speakers, video cards, graphics accelerators, and microphones, for example.

The device 170 may also include one or more modules. In general, the word "module," as used herein, refers to logic embodied in hardware or firmware, or to a collection of software instructions, possibly having entry and exit points, written in any programming language, such as, for example, Java, Python, Perl, Lua, C, C++, C#, etc. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, or any other tangible medium. Such software code may be stored, partially or fully, on a memory device of the executing computing device, such as the device 170, for execution by the computing device. It will be further appreciated that hardware modules may be comprised of connected logic units, such as gates and flip-flops, and/or may be comprised of programmable units, such as programmable gate arrays or processors.

Variations to the Disclosed Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for determining a distance and direction between a probe and a magnetic marker, the method comprising:
    providing the probe, wherein the probe comprises
        a first sensor including a first magnetometer having a first range within which a magnetic marker can be detected and a first accelerometer, and
        a second sensor including a second magnetometer having a second range within which the magnetic marker can be detected and a second accelerometer,
        wherein the first sensor is separated from the second sensor by a distance that is greater than the first range and the second range such that the magnetic marker can only be detected by one of the first magnetometer and the second magnetometer at a time;
        wherein the probe is configured to determine a position, in three-dimensional space, of the magnetic marker;
    balancing the probe while the probe is positioned away from the magnetic marker such that the magnetic marker is not within the first range of the first magnetometer or the second range of the second magnetometer;
    moving the balanced probe so that the magnetic marker is within the first range of the first magnetometer and not within the second range of the second magnetometer; and
    determining the distance and direction between the probe and the magnetic marker by comparing an output of the first sensor with an output of the second sensor.

2. The method of claim 1, wherein balancing the probe comprises compensating for a gain and an offset in an output of the first magnetometer and an output of the second magnetometer, wherein the gain and the offset are caused by hard and soft iron effects.

3. The method of claim 2, wherein the output of each of the first and second magnetometers comprises X, Y, and Z, values, and balancing the probe further comprises:
    rotating the probe through 360 degrees around each of three orthogonal axes;
    for each of the first and second magnetometers:
        recording minimum and maximum X, Y, and Z values output during the rotation;
        calculating a length between the recorded minimum and maximum X, Y, and Z values for each of X, Y, and Z;
        calculating a gain factor by dividing the length for each of X, Y, and Z by the average length of X, Y, and Z;
        calculating an offset value for each of X, Y, and Z by, for each of X, Y, and Z, adding half the length of X, Y, and Z, to the minimum value for X, Y, and Z.

4. The method of claim 3, further comprising adjusting raw output data into balanced output data by subtracting the offset value from the raw output data and multiplying by the gain factor for each of X, Y, and Z.

5. The method of claim 2, wherein the output of the first sensor comprises first magnetometer output data and first accelerometer output data, and the output of the second sensor comprises second magnetometer output data and second accelerometer output data, and wherein determining the distance and direction between the probe and the magnetic marker further comprises:
    calculating a difference between the first magnetometer output data and the second magnetometer output data to determine distance between the probe and the magnetic marker; and
    determining an orientation of the probe using one of the first accelerometer data or the second accelerometer data.

6. The method of claim 5, wherein the difference represents a field strength of the magnetic marker at a location of the probe, and wherein determining the distance between the probe and the magnetic marker comprises looking up the distance in a look up table based upon the field strength.

7. The method of claim 1, further comprising marking a location with the magnetic marker.

8. The method of claim 7, wherein the location is a location of a breast tumor to be surgically removed.

9. The method of claim 7, where the location is one of a location of a lung nodule, a lymph node, a parathyroid nodule, a thyroid nodule, or a GI lesion.

10. The method of claim 1, further comprising inserting the magnetic marker into a patient's body.

11. The method of claim 10, wherein the magnetic marker is coated in a layer of gold.

12. The method of claim 1, wherein the distance separating the first sensor and the second sensor is greater than the sum of the first range and the second range.

13. The method of claim 1, wherein the probe comprises:
    a base configured as a handle; and
    an extension portion extending from the base,
    wherein the first sensor is positioned in a distal tip of the extension portion, and the second sensor is positioned in the base.

14. The method of claim 1, wherein, when balanced and positioned such that the magnetic marker is not within the first range of the first magnetometer or the second range of the second magnetometer, an output of the first sensor comprises an ambient magnetic field strength, and an output of the second sensor also comprises the ambient magnetic field strength.

15. The method of claim 14, wherein, when balanced and positioned such that the magnetic marker is within the first range of the first magnetometer and not within the second range of the second magnetometer, the output of the first sensor comprises the ambient magnetic field strength plus a magnetic field strength due to the magnetic marker, and the output of the second sensor comprises the ambient magnetic field strength.

* * * * *